(12) United States Patent
Eckhardt et al.

(10) Patent No.: US 10,550,127 B1
(45) Date of Patent: Feb. 4, 2020

(54) INDANYLAMINOAZADIHYDRO-BENZOFURANYLACETIC ACIDS, PHARMACEUTICAL COMPOSITIONS FOR THE TREATMENT OF DIABETES

(71) Applicant: Boehringer Ingelheim International GmbH, Ingelheim am Rhein (DE)

(72) Inventors: Matthias Eckhardt, Biberach an der Riss (DE); Holger Wagner, Mettenberg (DE); Stefan Peters, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/484,124

(22) PCT Filed: Feb. 2, 2018

(86) PCT No.: PCT/EP2018/052620
§ 371 (c)(1),
(2) Date: Aug. 7, 2019

(87) PCT Pub. No.: WO2018/146008
PCT Pub. Date: Aug. 16, 2018

(30) Foreign Application Priority Data

Feb. 8, 2017 (EP) .................................. 17155191

(51) Int. Cl.
C07D 491/048 (2006.01)
A61K 45/06 (2006.01)

(52) U.S. Cl.
CPC .......... *C07D 491/048* (2013.01); *A61K 45/06* (2013.01); *C07B 2200/07* (2013.01)

(58) Field of Classification Search
CPC .. C07D 491/048; A61K 45/06; C07B 2200/07
USPC .................................................. 514/255.05
See application file for complete search history.

(56) References Cited

U.S. PATENT DOCUMENTS

| 2,505,322 | A | 4/1950 | Takeda |
| 2,560,111 | A | 7/1951 | Takeda |
| 2,656,003 | A | 10/1953 | Takeda |
| 7,799,782 | B2 | 9/2010 | Munson et al. |
| 2,727,340 | A1 | 1/2012 | Daiichi Sankyo |
| 8,222,281 | B2 | 7/2012 | Toda et al. |
| 8,633,182 | B2 | 1/2014 | Hamprecht et al. |
| 8,642,585 | B2 | 2/2014 | Eckhardt |
| 2006/0258722 | A1 | 11/2006 | Yasuma et al. |
| 2007/0033002 | A1 | 2/2007 | Dymetman et al. |
| 2010/0152165 | A1 | 6/2010 | Negoro et al. |
| 2011/0190330 | A1 | 8/2011 | Brown et al. |
| 2012/0172351 | A1 | 7/2012 | Negoro et al. |
| 2012/0302566 | A1 | 11/2012 | Himmelsbach et al. |
| 2013/0196998 | A1 | 8/2013 | Stoit et al. |
| 2013/0324514 | A1 | 12/2013 | Hamprecht et al. |
| 2014/0148462 | A1 | 5/2014 | Eckhardt |
| 2014/0163025 | A1 | 6/2014 | Eckhardt et al. |
| 2016/0009677 | A1 | 1/2016 | Lee et al. |
| 2016/0235706 | A1 | 8/2016 | Eckhardt et al. |

FOREIGN PATENT DOCUMENTS

| EP | 559422 | A1 | 9/1993 |
| EP | 1630152 | A1 | 3/2006 |
| EP | 1916234 | A1 | 4/2008 |
| EP | 2006271 | A2 | 12/2008 |
| EP | 2096109 | A1 | 9/2009 |
| EP | 2289868 | A1 | 3/2011 |
| JP | 2009542580 | | 1/2012 |
| JP | 2012529422 | A | 11/2012 |
| WO | 2004041266 | A1 | 5/2004 |
| WO | 2005051890 | A1 | 6/2005 |
| WO | 2005087710 | A1 | 9/2005 |

(Continued)

OTHER PUBLICATIONS

Mikami, et al., "Discovery of Phenylpropanoic Acid Derivatives Containing Polar Functionalities as Potent and Orally Bioavailable G Protein-Coupled Receptor 40 Agonists for the Treatment of Type 2 Diabetes", Journal of Medicinal Chemistry, 2012, V. 55, No. 8, p. 3756-3776.
International Search Report and written opinion for PCT/EP 2013/058840 dated Aug. 22, 2013.
Mikami, Satoshi et al. "Discovery of Phenylpropanoic Acid Derivatives Containing Polar Functionalities as Potent and Orally Bioavailable G Protein-Coupled Receptor 40 Agonists for the Treatment of Type 2 Diabetes" Journal of Medicinal Chemistry (2012) 55, 3756-3776.
Negoro, Nobuyuki et al. "Identification of Fused-Ring Alkanoic Acids with Improved Pharmacokinetic Profiles that Act as G Protein-Coupled Receptor 40/ Free Fatty Acid Receptor 1 Agonists" Journal of Medicinal Chemistry, (2012) 55, pp. 1538-1552.
International Search Report for PCT/EP2013/056312 dated May 27, 2013.

(Continued)

*Primary Examiner* — Kristin A Vajda
(74) *Attorney, Agent, or Firm* — David L. Kershner

(57) ABSTRACT

The present invention relates to compounds of general formula I,

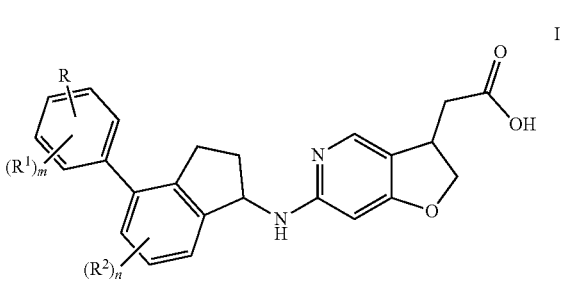

wherein the groups R, $R^1$, $R^2$, m and n are defined herein, which have valuable pharmacological properties, in particular bind to the GPR40 receptor and modulate its activity. The compounds are suitable for treatment and prevention of diseases which can be influenced by this receptor, such as metabolic diseases, in particular diabetes type 2. Furthermore, the invention relates to novel intermediates, useful for the synthesis of compounds of formula I.

14 Claims, No Drawings

(56) References Cited

FOREIGN PATENT DOCUMENTS

| WO | 2007033002 | A1 | 3/2007 |
| WO | 2008001931 | A2 | 1/2008 |
| WO | 2009157418 | A1 | 12/2009 |
| WO | 201043733 | A1 | 4/2010 |
| WO | 2010045258 | A2 | 4/2010 |
| WO | 2010143733 | A1 | 12/2010 |
| WO | 2012072691 | A1 | 6/2012 |
| WO | 2013144098 | A1 | 10/2013 |
| WO | 2013178575 | A1 | 12/2013 |
| WO | 2014019186 | A1 | 2/2014 |
| WO | 2015024526 | A1 | 2/2015 |
| WO | 2018138029 | A1 | 8/2018 |
| WO | 2018146008 | A1 | 8/2018 |

OTHER PUBLICATIONS

Itoh, et al., Free fatty acids regulate insulin secretion from pancreatic b cells through GPR40 , Letters to Nature, 2003, vol. 422, p. 173-176.

Briscoe, et al., "The Orphan G Protein-coupled Receptor GPR40 is activated by Medium and Long Chain Fatty Acids", Journal of Biological Chemistry, vol. 278, No. 13, 2003, p. 11303-11311.

Kotarsky, et al., "A human cell surface receptor activated by free fatty acids and thiazolidine drugs", Biochemical and Biophysical Research Communications, vol. 301, No. 2, 2003, p. 406-410.

Song et al., "Synthesis and Biological Evaluation of 3-Aryl-3-(4-phenoxy)-propionic Acid as a Novel Series of G Protein-Coupled Receptor 40 Agonists", Journal of Medicinal Chemistry, vol. 50, 2007, p. 2807-2817.

Tan, et al., "Selective Small-Molecule Agonists of G Protein-coupled Receptor 40 Promote Glucose-Dependent Insulin Secretion and Reduce Blood Glucose in Mice", Diabetes, vol. 57, 2008, p. 2211.

International Search Report, PCT/EP2013072238, dated Jan. 22, 2014.

International Search Report and Written Opinion, PCT/EP 2013/0744386, dated Jan. 16, 2014.

International Search Report for PCT/EP2018/051387 dated Mar. 15, 2018.

Takano, Discovery of 3-aryl-3-ethoxypropanoic acids as orally active GPR40 agonists, Bioorganic and Medicinak Chem Letters, vol. 24, p. 2949-2953, 2014.

Written Opinion for PCT/EP2018/051387 dated Mar. 18, 2018.

International Search Report for PCT/EP2018/051384 dated Mar. 15, 2018.

Written Opinion for PCT/EP2018/051384 dated Mar. 15, 2018.

International Search report for PCT/EP2018/051385 dated Mar. 15, 2018.

Written Opinion for PCT/EP2018/051385 dated Mar. 15, 2018.

International Search Report for PCT/EP2018/052620 dated Apr. 4, 2018.

Written Opinion for PCT/EP2018052620 dated Apr. 4, 2018.

International Search report and Written opinion for PCT/EP2016/070839, dated Oct. 14, 2016.

INDANYLAMINOAZADIHYDRO-BENZOFURANYLACETIC ACIDS, PHARMACEUTICAL COMPOSITIONS FOR THE TREATMENT OF DIABETES

FIELD OF THE INVENTION

The present invention relates to novel indanylaminoazadihydrobenzofuranylacetic acids, that are agonists of the G-protein coupled receptor 40 (GPR40, also known as free fatty acid receptor FFAR 1), to processes for their preparation, to intermediates for their preparation, to pharmaceutical compositions containing these compounds and to their medical use for the prophylaxis and/or treatment of diseases which can be influenced by the modulation of the function of GPR40. Particularly, the pharmaceutical compositions of the invention are suitable for the prophylaxis and/or therapy of metabolic diseases, such as diabetes, more specifically type 2 diabetes mellitus, and conditions associated with the disease, including insulin resistance, obesity, cardiovascular disease and dyslipidemia.

BACKGROUND OF THE INVENTION

Metabolic diseases are diseases caused by an abnormal metabolic process and may either be congenital due to an inherited enzyme abnormality or acquired due to a disease of an endocrine organ or failure of a metabolically important organ such as the liver or the pancreas.

Diabetes mellitus is a disease state or process derived from multiple causative factors and is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia).

Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Persistent or inadequately controlled hyperglycemia is associated with a wide range of pathologies. Diabetes is a very disabling disease, because today's common antidiabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, stroke, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

The free fatty acid receptor GPR40 (also referred to as either FFAR, FFAR1, or FFA1) is a cell-surface receptor and a member of the gene superfamily of G-protein coupled receptors, which was first identified as a so-called orphan receptor, i.e. a receptor without a known ligand, based on the predicted presence of seven putative transmembrane regions in the corresponding protein (Sawzdargo et al. (1997) Biochem. Biophys. Res. Commun. 239: 543-547). GPR40 is found to be highly expressed in several particular cell types: the pancreatic 3 cells and insulin-secreting cell lines, as well as in enteroendocrine cells, taste cells, and is reported to be expressed in immune cells, splenocytes, and in the human and monkey brain. Meanwhile, fatty acids of varying chain lengths are thought to represent the endogenous ligands for GPR40, activation of which is linked primarily to the modulation of the Gq family of intra-cellular signaling G proteins and concomitant induction of elevated calcium levels, although activation of Gs- and Gi-proteins to modulate intracellular levels of cAMP have also been reported. GPR40 is activated especially by long-chain FFA, particularly oleate, as well as the PPAR-gamma agonist rosiglitazone.

It has been recognized that the fatty acids that serve as activators for GPR40 augment the elevated plasma glucose-induced secretion of insulin through GPR40 receptors that are expressed in the insulin secreting cells (Itoh et al. (2003) Nature 422: 173-176; Briscoe et al. (2003) J. Biol. Chem. 278: 11303-11311; Kotarsky et al. (2003) Biochem. Biophys. Res. Commun. 301: 406-410). Despite initial controversy, the use of GPR40 agonist appears to be the appropriate for increasing insulin release for the treatment of diabetes (see e.g. Diabetes 2008, 57, 2211; J. Med. Chem. 2007, 50, 2807). Typically, long term diabetes therapy leads to the gradual diminution of islet activity, so that after extended periods of treatment Type 2 diabetic patients need treatment with daily insulin injections instead. GPR40 agonists may have the potential to restore or preserve islet function, therefore, GPR40 agonists may be beneficial also in that that they may delay or prevent the diminution and loss of islet function in a Type 2 diabetic patient.

It is well established that the incretins GLP-1 (glucagon-like peptide-1) and GIP (glucose-dependent insulinotropic peptide; also known as gastric inhibitory peptide) stimulate insulin secretion and are rapidly inactivated in vivo by DPP-4. These peptidyl hormones are secreted by endocrine cells that are located in the epithelium of the small intestine. When these endocrine cells sense an increase in the concentration of glucose in the lumen of the digestive tract, they act as the trigger for incretin release. Incretins are carried through the circulation to beta cells in the pancreas and cause the beta cells to secrete more insulin in anticipation of an increase of blood glucose resulting from the digesting meal. Further studies indicating that the GPR40 modulatory role on the release of incretins from the enteroendocrine cells, including CCK, GLP-1, GIP, PYY, and possibly others, suggest that GPR40 modulators may contribute to enhanced insulin release from the pancreatic beta cells also indirectly by e.g. a synergistic effect of GLP-1 and possibly GIP on the insulin release, and the other release incretins may also contribute to an overall beneficial contribution of GPR40 modulation on metabolic diseases. The indirect contributions of GPR40 modulation on insulin release through the elevation of plasma levels of incretins may be further augmented by the coadministration of inhibitors of the enzymes responsible for the incretin degradation, such as inhibitors of DPP-4.

Insulin imbalances lead to conditions such as type II diabetes mellitus, a serious metabolic disease. The modulation of the function of GPR40 in modulating insulin secretion indicates the therapeutic agents capable of modulating GPR40 function could be useful for the treatment of disorders such as diabetes and conditions associated with the disease, including insulin resistance, obesity, cardiovascular disease and dyslipidemia.

OBJECT OF THE PRESENT INVENTION

The object of the present invention is to provide new compounds, hereinafter described as compounds of formula I, in particular new indanylaminoazadihydrobenzofuranylacetic acids, which are active with regard to the G-protein-coupled receptor GPR40, notably are agonists of the G-protein-coupled receptor GPR40.

A further object of the present invention is to provide new compounds, in particular new indanylaminoazadihydrobenzofuranylacetic acids, which have an activating effect on the G-protein-coupled receptor GPR40 in vitro and/or in vivo and possess suitable pharmacological and pharmacokinetic properties to use them as medicaments.

A further object of the present invention is to provide effective GPR40 agonists, in particular for the treatment of metabolic disorders, for example diabetes, dyslipidemia and/or obesity.

A further object of the present invention is to provide methods for treating a disease or condition mediated by the activation the G-protein-coupled receptor GPR40 in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

GPR40 modulators are known in the art, for example, the compounds disclosed in WO 2004/041266 (EP 1 559 422), WO 2007/033002, WO 2009/157418, and WO 2013/178575. The indanylaminoazadihydrobenzofuranylacetic acids of the present invention may provide several advantages, such as enhanced potency, high metabolic and/or chemical stability, high selectivity and tolerability, enhanced solubility, and the possibility to form stable salts.

SUMMARY OF THE INVENTION

In a first aspect, the invention relates to a compound of formula

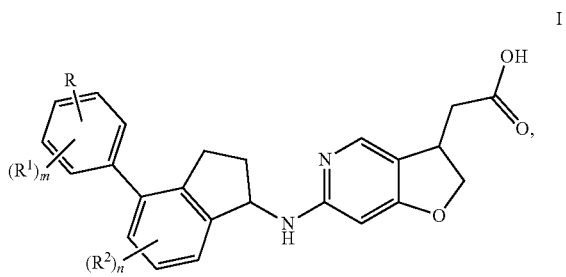

wherein
R is selected from the group R-G1 consisting of
H, F, Cl, Br, I, $C_{1-6}$-alkyl, $C_{2-6}$-alkenyl, $C_{2-6}$-alkynyl, $C_{3-6}$-cycloalkyl, NC—, $HNR^N$—C(=O)—, $C_{1-4}$-alkyl-$NR^N$—C(=O)—, $C_{3-6}$-cycloalkyl-$NR^N$—C(=O)—, heterocyclyl-$NR^N$—C(=O)—, heteroaryl-$NR^N$—C(=O)—, HOOC—, $C_{1-4}$-alkyl-O—C(=O)—, $O_2N$—, $HR^NN$—, $C_{1-4}$-alkyl-$R^NN$—, $C_{1-4}$-alkyl-C(=O)$NR^N$—, $C_{3-6}$-cycloalkyl-C(=O)$NR^N$—, heterocyclyl-C(=O)—$NR^N$—, heteroaryl-C(=O)$NR^N$—, $C_{1-4}$-alkyl-S(=O)$_2NR^N$—, $C_{3-6}$-cycloalkyl-S(=O)$_2$$NR^N$—, heterocyclyl-S(=O)$_2NR^N$—, heteroaryl-S(=O)$_2NR^N$—, HO—, $C_{1-6}$-alkyl-O—, HOOC—$C_{1-3}$-alkyl-O—, heterocyclyl-$C_{1-3}$-alkyl-O—, phenyl-$C_{1-3}$-alkyl-O—, $C_{3-6}$-cycloalkyl-O—, heterocyclyl-O—, heteroaryl-O—, $C_{1-4}$-alkyl-S—, $C_{3-6}$-cycloalkyl-S—, heterocyclyl-S—, $C_{1-4}$-alkyl-S(=O)—, $C_{3-6}$-cycloalkyl-S(=O)—, heterocyclyl-S(=O)—, $C_{1-4}$-alkyl-S(=O)$_2$—, $C_{3-6}$-cycloalkyl-S(=O)$_2$—, heterocyclyl-S(=O)$_2$—, phenyl-S(=O)$_2$—, heteroaryl-S(=O)$_2$—, $HNR^N$—S(=O)$_2$—, $C_{1-4}$-alkyl-$NR^N$—S(=O)$_2$—, heterocyclyl, phenyl, and heteroaryl,
wherein each alkyl, cycloalkyl, and heterocyclyl group or sub-group within the group of residues mentioned for R is optionally substituted with 1 or more F atoms and optionally substituted with 1 to 3 groups independently selected from Cl, $C_{1-3}$-alkyl, NC—, $(R^N)_2N$—, HO—, $C_{1-3}$-alkyl-O—, and $C_{1-3}$-alkyl-S(=O)$_2$—; and
wherein each phenyl and heteroaryl group or sub-group within the group of residues mentioned for R is optionally substituted with 1 to 5 substituents independently selected from F, Cl, $C_{1-3}$-alkyl, $HF_2C$—, $F_3C$—, NC—, $(R^N)_2N$—, HO—, $C_{1-3}$-alkyl-O—, $F_3C$—O—, and $C_{1-3}$-alkyl-S(=O)$_2$—;
wherein each heterocyclyl group or sub-group within the group of residues mentioned for R is selected from
a cyclobutyl group wherein 1 CH$_2$ group is replaced by —$NR^N$— or —O—;
a $C_{5-6}$-cycloalkyl group wherein 1 CH$_2$ group is replaced by —C(=O)—, —$NR^N$—, —O—, —S—, or —S(=O)$_2$— and/or 1 CH group is replaced by N;
a $C_{5-6}$-cycloalkyl group wherein 1 CH$_2$ group is replaced by —$NR^N$— or —O—, a second CH$_2$ group is replaced by —$NR^N$—, —C(=O)— or —S(=O)$_2$— and/or 1 CH group is replaced by N; and
a $C_{5-6}$-cycloalkyl group wherein 2 CH$_2$ groups are replaced by —$NR^N$— or 1 CH$_2$ group by —$NR^N$— and the other by —O— and a third CH$_2$ group is replaced by —C(=O)— or —S(=O)$_2$— and/or 1 CH group is replaced by N;
wherein each heteroaryl group or sub-group within the group of residues mentioned for R is selected from tetrazolyl and a 5- or 6-membered heteroaromatic ring which contains 1, 2, or 3 heteroatoms independently of each other selected from =N—, —NR$^N$—, —O—, and —S—, wherein in heteroaromatic groups containing a —HC=N— unit this group is optionally replaced by —NR$^N$—C(=O)—;

wherein in heteroaryl and heterocyclyl rings with one or more NH groups, each of said NH groups is replaced by NR$^N$;

R$^1$ is selected from the group R$^1$-G1 consisting of H, F, Cl, C$_{1-4}$-alkyl, C$_{3-6}$-cycloalkyl-, HO—C$_{1-4}$-alkyl, C$_{1-4}$-alkyl-O—C$_{1-4}$-alkyl, NC—, HO—, C$_{1-4}$-alkyl-O—, C$_{3-6}$-cycloalkyl-O—, C$_{1-4}$-alkyl-S—, C$_{1-4}$-alkyl-S(O)—, and C$_{1-4}$-alkyl-S(O)$_2$—, wherein any alkyl and cycloalkyl group or sub-group within the group of residues mentioned for R$^1$ is optionally substituted with 1 or more F atoms, and wherein multiple R$^1$ may be identical or different if m is 2, 3 or 4;

m is an integer selected from 1, 2, 3, and 4;

R$^2$ is selected from the group R$^2$-G1 consisting of H, F, Cl, C$_{1-4}$-alkyl, NC—, and C$_{1-4}$-alkyloxy, wherein any alkyl group or sub-group within the group of residues mentioned for R$^2$ is optionally substituted with 1 or more F atoms, and wherein multiple R$^2$ may be identical or different if n is 2 or 3;

n is an integer selected from 1, 2, and 3;

R$^N$ is independently of each other selected from the group R$^N$-G1 consisting of H, C$_{1-4}$-alkyl, HO—C$_{1-4}$-alkyl-(H$_2$C)—, C$_{1-3}$-alkyl-O—C$_{1-4}$-alkyl-, C$_{1-4}$-alkyl-C(=O)—, C$_{1-4}$-alkyl-NH—C(=O)—, C$_{1-4}$-alkyl-N(C$_{1-4}$-alkyl)-C(=O)—, C$_{1-4}$-alkyl-O—C(=O)—, and C$_{1-4}$-alkyl-S(=O)$_2$—, wherein each alkyl group or sub-group within the group of residues mentioned for R$^N$ is optionally substituted with 1 or more F atoms;

wherein in any definition mentioned hereinbefore and if not specified otherwise, any alkyl group or sub-group may be straight-chained or branched, the isoforms, tautomers, stereoisomers, metabolites, prodrugs, solvates, hydrates, and the salts thereof, particularly the physiologically acceptable salts thereof with inorganic or organic acids or bases, or the combinations thereof.

The extension -Gn used within the definitions is meant to identify genus n of the respective substituent. For example, R-G1 defines genus 1 of the substituent R.

The expression "optionally substituted with 1 or more F atoms" means that none or one up to successively all H atoms bound to carbon atoms of the respective group or submoiety may be replaced by F atoms, preferably 1 to 5H atoms or, more preferred, 1 to 3H atoms may be replaced by F atoms.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the G-protein-coupled receptor GPR40 in a patient in need thereof characterized in that a compound of general formula I or a pharmaceutically acceptable salt thereof is administered to the patient.

According to another aspect of the invention, there is provided a method for treating a metabolic disease or disorder, such as diabetes, dyslipidemia and/or obesity, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the G-protein-coupled receptor GPR40 in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the activation of the G-protein-coupled receptor GPR40.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly R, R$^1$, R$^2$, m and n are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

R:

R-G1:

The group R is preferably selected from the group R-G1 as defined hereinbefore.

R-G2:

In another embodiment, the group R is selected from the group R-G2 consisting of H, F, Cl, C$_{1-6}$-alkyl, C$_{3-6}$-cycloalkyl, NC—, HNR$^N$—C(=O)—, C$_{1-4}$-alkyl-NR$^N$—C(=O)—, C$_{3-6}$-cycloalkyl-NR$^N$—C(=O)—, heterocyclyl-NR$^N$—C(=O)—, HOOC—, HR$^N$N—, C$_{1-4}$-alkyl-R$^N$N—, C$_{1-4}$-alkyl-C(=O)NR$^N$—, C$_{3-6}$-cycloalkyl-C(=O)NR$^N$—, heterocyclyl-C(=O)NR$^N$—, C$_{1-4}$-alkyl-S(=O)$_2$NR$^N$—, HO—, C$_{1-6}$-alkyl-O—, HOOC—(C$_{1-2}$-alkyl)-O—, heterocyclyl-C$_{1-2}$-alkyl-O—, phenyl-C$_{1-2}$-alkyl-O—, C$_{3-6}$-cycloalkyl-O—, heterocyclyl-O—, heteroaryl-O—, C$_{1-4}$-alkyl-S(=O)$_2$—, C$_{3-6}$-cycloalkyl-S(=O)$_2$—, heterocyclyl-S(=O)$_2$—, HNR$^N$—S(=O)$_2$-, C$_{1-4}$-alkyl-NR$^N$—S(=O)$_2$—, heterocyclyl, and heteroaryl, wherein each alkyl, cycloalkyl, and heterocyclyl group or sub-group within the group of residues mentioned for R is optionally substituted with 1 or more F atoms and optionally substituted with 1 to 2 groups independently selected from Cl, $H_3C$—, NC—, $R^N HN$—, HO—, $H_3C$—O—, and $H_3C$—S(=O)$_2$—;

wherein each heteroaryl group or sub-group within the group of residues mentioned for R is optionally substituted with 1 to 3 substituents independently selected from F, Cl, $H_3C$—, $F_3C$—, NC—, $(R^N)_2N$—, HO—, $H_3C$—O—, $F_3C$—O—, and $H_3C$—S(=O)$_2$—;

wherein each heterocyclyl group or sub-group within the group of residues mentioned for R is selected from
a cyclobutyl group wherein 1 $CH_2$ group is replaced by —$NR^N$— or —O—;
a $C_{5-6}$-cycloalkyl group wherein 1 $CH_2$ group is replaced by —C(=O)—, —$NR^N$—, —O—, —S— or —S(=O)$_2$— and/or 1 CH group is replaced by N;
a $C_{5-6}$-cycloalkyl group wherein 1 $CH_2$ group is replaced by —$NR^N$— or —O—, a second $CH_2$ group is replaced by —$NR^N$—, —C(=O)— or —S(=O)$_2$— and/or 1 CH group is replaced by N;

wherein each heteroaryl group or sub-group within the group of residues mentioned for R is selected from
tetrazolyl, a 5-membered heteroaromatic ring which contains 1, 2 or 3 heteroatoms independently of each other selected from =N—, —NH—, O and S, and a 6-membered heteroaromatic ring which contains 1 or 2 =N— atoms, wherein a —HC=N— unit is optionally replaced by —NH—C(=O)—;

and wherein in each of the above heteroaryl and heterocyclyl group or sub-group containing one or more NH, said NH group(s) is/are replaced by $NR^N$.

R-G3:

In another embodiment, the group R is selected from the group R-G3 consisting of H, F, Cl, $C_{1-4}$-alkyl, $C_3$-cycloalkyl, NC—, $H_2N$—C(=O)—, $C_{1-3}$-alkyl-$NR^N$—C(=O)—, HOOC—, $H_2N$—, $C_{1-3}$-alkyl-C(=O)$NR^N$—, $C_{1-4}$-alkyl-S(=O)$_2NR^N$—, HO—, $C_{1-5}$-alkyl-O—, HOOC—$CH_2$—O—, heterocyclyl-$CH_2$—O—, phenyl-$CH_2$—O—, $C_{3-6}$-cycloalkyl-O—, heterocyclyl-O—, heteroaryl-O—, heterocyclyl-S(=O)$_2$—, heterocyclyl, and heteroaryl, wherein each alkyl, cycloalkyl, and heterocyclyl group or sub-group within the group of residues mentioned for R is optionally substituted with 1 or more F atoms and optionally substituted with 1 group selected from Cl, $H_3C$—, NC—, $R^N HN$—, HO—, $H_3C$—O—, and $H_3C$—S(=O)$_2$—;

wherein each heteroaryl group or sub-group within the group of residues mentioned for R is optionally substituted with 1 to 2 substituents independently selected from F, Cl, $H_3C$—, $F_3C$—, NC—, $(R^N)_2N$—, HO—, $H_3C$—O—, $F_3C$—O—, and $H_3C$—S(=O)$_2$—;

wherein each heterocyclyl or sub-group within the group of residues mentioned for R is selected from
a cyclobutyl group wherein 1 $CH_2$ group is replaced by —$NR^N$— or —O—;
a $C_{5-6}$-cycloalkyl group wherein 1 $CH_2$ group is replaced by —C(=O)—, —$NR^N$—, —O—, —S— or —S(=O)$_2$— and/or 1 CH group is replaced by N;

wherein each heteroaryl group or sub-group within the group of residues mentioned for R is selected from
tetrazolyl, a 5-membered heteroaromatic ring which contains 1, 2 or 3 heteroatoms independently of each other selected from =N—, —NH—, O and S, and a 6-membered heteroaromatic ring which contains 1 or 2 =N— atoms, wherein a —HC=N— unit is optionally replaced by —NH—C(=O)—;

and wherein in each heteroaryl and heterocyclyl group or sub-group mentioned for R containing one or more NH, said NH group(s) is/are replaced by $NR^N$.

R-G4:

According to another embodiment, the group R is selected from the group R-G4 consisting of
$H_3C$—O— monosubstituted with $C_{1-4}$-alkyl, oxetanyl, or tetrahydrofuranyl,
wherein the $C_{1-4}$-alkyl group attached to $H_3C$—O— is optionally monosubstituted with HO—, and
wherein said oxetanyl and tetrahydrofuranyl are optionally monosubstituted with $H_3C$—;
tetrahydrofuranyl-O— and tetrahydropyranyl-O—; and
a heteroaryl group selected from tetrazolyl, pyridin-2-onyl, pyrazinyl, pyrimidin-2-onyl, and pyrimidin-4-onyl,
wherein each of said heteroaryl groups is optionally monosubstituted with $H_3C$—, and
wherein each H—N group in said heteroaryl groups is optionally replaced with $H_3C$—N or $(H_3C)_2C(OH)$—$H_2C$—N.

R-G5:

In another embodiment, the group R is selected from the group R-G5 consisting of

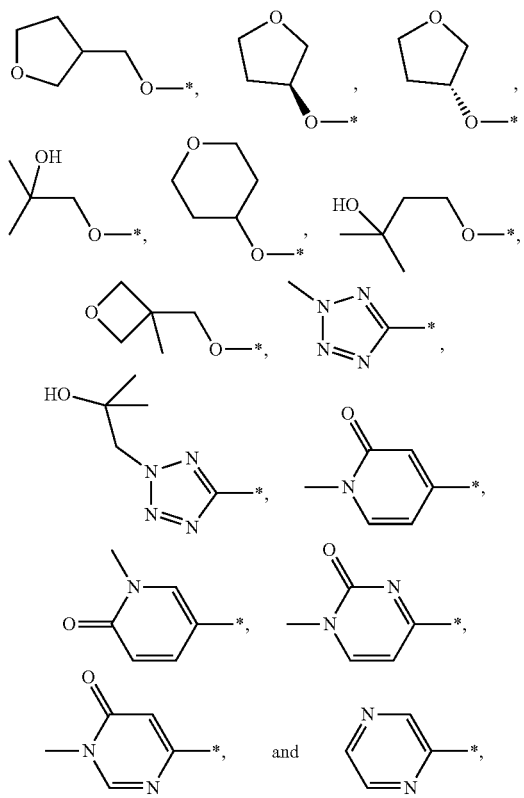

wherein the asterisk (-*) indicates the site/point of attachment.

$R^1$:

$R^1$-G1:

The group $R^1$ is preferably selected from the group $R^1$-G1 as defined hereinbefore.

R¹-G2:

According to one embodiment the group R¹ is selected from the group R¹-G2 consisting of H, F, Cl, $C_{1-3}$-alkyl, cyclopropyl, NC—, HO—, and $C_{1-3}$-alkyl-O—,
  wherein each alkyl group or sub-group within the group of residues mentioned for R¹ is optionally substituted with 1 or more F atoms.

R¹-G3:

According to one embodiment, the group R¹ is selected from the group R¹-G3 consisting of H, F, Cl, $H_3C$—, $H_3C$—$H_2C$—, $(H_3C)_2CH$—, $F_3C$—, and $H_3C$—O—.

R¹-G4:

According to one embodiment, the group R¹ is selected from the group R¹-G4 consisting of $H_3C$—.

R²:

R²-G1:

The group R² is preferably selected from the group R²-G1 as defined hereinbefore.

R²-G2:

In another embodiment, the group R² is selected from the group R²-G2 consisting of H, F, Cl, $H_3C$—, $F_3C$—, NC—, and $H_3CO$—.

R²-G3:

In another embodiment, the group R² is selected from the group R²-G3 consisting of H and F.

R²-G4:

In another embodiment, the group R² is selected from the group R²-G4 consisting of H.

R²-G5:

In another embodiment, the group R² is selected from the group R²-G5 consisting of F.

$R^N$:

$R^N$-G1:

The group $R^N$ is preferably selected from the group $R^N$-G1 as defined hereinbefore.

$R^N$-G2:

In another embodiment, the group $R^N$ is selected from the group $R^N$-G2 consisting of H, $C_{1-3}$-alkyl, HO—$C_{1-4}$-alkyl-$(H_2C)$—, $H_3C$—O—$C_{1-4}$-alkyl-, $C_{1-3}$-alkyl-C(=O)—, and $C_{1-3}$-alkyl-S(=O)_2$—.

$R^N$-G3:

In another embodiment, the group $R^N$ is selected from the group $R^N$-G3 consisting of H, $H_3C$—, HO—$C_3$-alkyl-$(H_2C)$—, $H_3C$—C(=O)—, and $H_3C$—S(=O)_2$—.

m:

m is an integer selected from 1, 2, 3 and 4.

Preferably, m is an integer selected from 1 and 2.

More preferably, m is 2.

n:

n is an integer selected from 1, 2 and 3.

Preferably, n is an integer selected from 1 and 2.

More preferably, n is 1.

The following preferred embodiments of compounds of the formula I are described using generic formulae I.1, I.2, I.3, and I.4, wherein any tautomers, solvates, hydrates and salts thereof, in particular the pharmaceutically acceptable salts thereof, are encompassed.

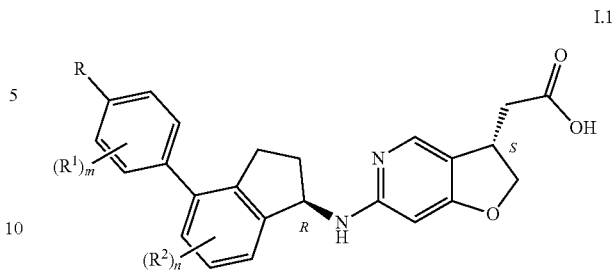

I.1

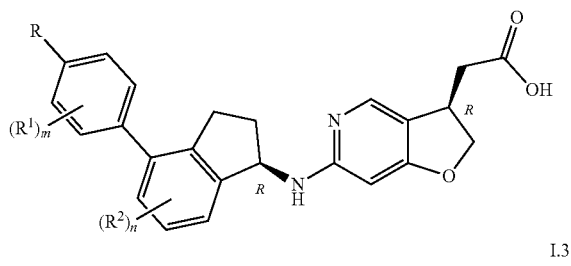

I.2

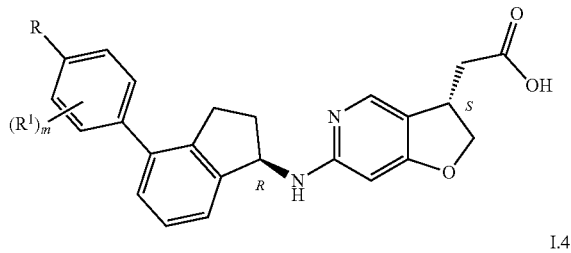

I.3

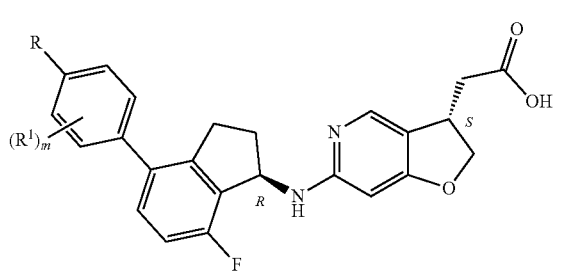

I.4

Examples of preferred subgeneric embodiments (E) according to the present invention are set forth in the following table 1, wherein each substituent group of each embodiment is defined according to the definitions set forth hereinbefore and wherein all other substituents of the formulae I, I.1, I.2, I.3, and I.4 are defined according to the definitions set forth hereinbefore. For example, the entry -G1 in the column under R— and in the line of E1 means that in embodiment E1, substituent R is selected from the definition designated R-G1. The same applies analogously to the other variables incorporated in the general formulae.

TABLE 1

| E  | R-  | R¹- | R²- | $R^N$- | m       | n     |
|----|-----|-----|-----|--------|---------|-------|
| E1 | -G1 | -G1 | -G1 | -G1    | 1,2,3,4 | 1,2,3 |
| E2 | -G1 | -G1 | -G1 | -G2    | 1,2     | 1,2   |
| E3 | -G1 | -G1 | -G1 | -G3    | 1,2     | 1,2   |
| E4 | -G1 | -G1 | -G2 | -G3    | 1,2     | 1,2   |
| E5 | -G1 | -G2 | -G2 | -G1    | 1,2     | 1,2   |
| E6 | -G1 | -G2 | -G2 | -G2    | 1,2     | 1,2   |
| E7 | -G1 | -G2 | -G2 | -G3    | 1,2     | 1,2   |
| E8 | -G2 | -G1 | -G1 | -G1    | 1,2     | 1,2   |

TABLE 1-continued

| E | R- | R¹- | R²- | R^N- | m | n |
|---|---|---|---|---|---|---|
| E9  | -G3 | -G1 | -G1 | -G1 | 1,2 | 1,2 |
| E10 | -G3 | -G1 | -G2 | -G2 | 1,2 | 1,2 |
| E11 | -G3 | -G2 | -G2 | -G2 | 1,2 | 1,2 |
| E12 | -G2 | -G2 | -G2 | -G3 | 1,2 | 1,2 |
| E13 | -G3 | -G2 | -G2 | -G3 | 1,2 | 1,2 |
| E14 | -G1 | -G3 | -G2 | -G3 | 1,2 | 1,2 |
| E15 | -G1 | -G2 | -G3 | -G3 | 1,2 | 1,2 |
| E16 | -G1 | -G3 | -G3 | -G3 | 1,2 | 1,2 |
| E17 | -G1 | -G4 | -G3 | -G3 | 1,2 | 1,2 |
| E18 | -G2 | -G3 | -G2 | -G3 | 1,2 | 1,2 |
| E19 | -G2 | -G2 | -G3 | -G3 | 1,2 | 1,2 |
| E20 | -G2 | -G3 | -G3 | -G3 | 1,2 | 1,2 |
| E21 | -G2 | -G4 | -G3 | -G3 | 1,2 | 1,2 |
| E22 | -G3 | -G3 | -G2 | -G3 | 1,2 | 1,2 |
| E23 | -G3 | -G2 | -G3 | -G3 | 1,2 | 1,2 |
| E24 | -G3 | -G3 | -G3 | -G3 | 1,2 | 1,2 |
| E25 | -G3 | -G4 | -G3 | -G3 | 1,2 | 1,2 |
| E26 | -G4 | -G3 | -G2 | — | 2 | 1,2 |
| E27 | -G4 | -G2 | -G3 | — | 2 | 1 |
| E28 | -G4 | -G3 | -G3 | — | 2 | 1 |
| E29 | -G4 | -G4 | -G3 | — | 2 | 1 |
| E30 | -G5 | -G3 | -G2 | — | 2 | 1,2 |
| E31 | -G5 | -G2 | -G3 | — | 2 | 1 |
| E32 | -G5 | -G3 | -G3 | — | 2 | 1 |
| E33 | -G5 | -G4 | -G3 | — | 2 | 1 |

Another embodiment concerns those compounds of formula I, wherein
R is selected from the group consisting of

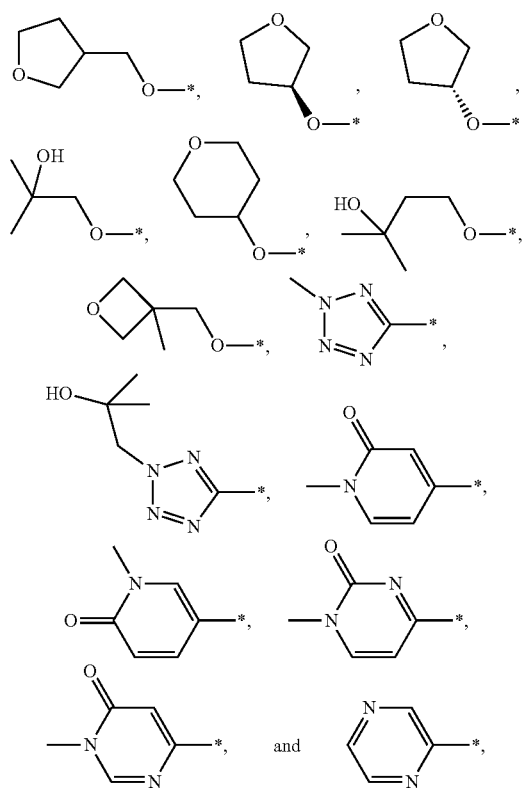

wherein the asterisk (-*) indicates the site/point of attachment;
R¹ is H₃C—;
m is 2;
R² is H or F;
n is 1.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis for example using methods described in "Comprehensive Organic Transformations", 2$^{nd}$ Edition, Richard C. Larock, John Wiley & Sons, 2010, and "March's Advanced Organic Chemistry", 7$^{th}$ Edition, Michael B. Smith, John Wiley & Sons, 2013. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to the skilled man and described in the literature for example in "Protecting Groups", 3$^{rd}$ Edition, Philip J. Kocienski, Thieme, 2005, and "Protective Groups in Organic Synthesis", 4$^{th}$ Edition, Peter G. M. Wuts, Theodora W. Greene, John Wiley & Sons, 2006.

The compounds of the invention I are preferably accessed from a precursor II that bears the carboxylic acid function in a protected or masked form as sketched in Scheme 1; R, R¹, R², m and n have the meanings as defined hereinbefore and hereinafter. Suited precursor groups for the carboxylic acid may be, e.g., a carboxylic ester, a carboxylic amide, cyano, an olefin, an oxazole, or a thiazole. All these groups have been transformed into the carboxylic acid function by different means which are described in the organic chemistry literature and are known to the one skilled in the art. The preferred precursor group is a $C_{1-4}$-alkyl or benzyl carboxylate, each of which may be additionally mono- or polysubstituted with fluorine, methyl, and/or methoxy. These ester groups may be hydrolyzed with an acid, such as hydrochloric acid or sulfuric acid, or an alkali metal hydroxide, such as lithium hydroxide, sodium hydroxide, or potassium hydroxide, to yield the carboxylic acid function. The hydrolysis is preferably conducted in aqueous solvents, such as water and tetrahydrofuran, 1,4-dioxane, alcohol, e.g., methanol, ethanol, and isopropanol, or dimethyl sulfoxide, at 0 to 120° C. A tert-butyl ester is preferably cleaved under acidic conditions, e.g., trifluoroacetic acid or hydrochloric acid, in a solvent such as dichloromethane, 1,4-dioxane, isopropanol, or ethyl acetate. A benzyl ester is advantageously cleaved using hydrogen in the presence of a transition metal, preferably palladium on carbon. Benzyl esters bearing electron donating groups, such as methoxy, on the aromatic ring may also be removed under oxidative conditions; ceric ammonium nitrate (CAN) or 2,3-dichloro-5,6-dicyanoquinone (DDQ) are two commonly used reagents for this approach. The carboxylic acid group may also be introduced at an earlier stage of the synthesis, e.g., prior to the coupling of the azadihydrobenzofuran part with the indanylamino residue or the C—C coupling of the two phenyl subgroups as described in the experimental section.

Scheme 1: Liberation of carboxylic acid function to access compounds of the invention

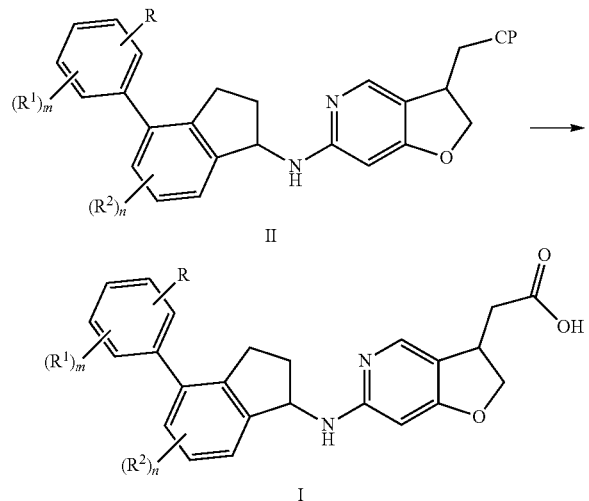

CP = masked or protected form of COOH, e.g., $CO_2C_{1-4}$-alkyl, $CO_2CH_2$aryl, $CON(C_{1-4}$-alkyl$)_2$, CN, CH=$CH_2$, thiazol-2-yl, oxazol-2-yl Compound II, in turn, may be obtained from indanylamine III and compound IV which bears the carboxylic acid group or a precursor group thereof and a leaving group (Scheme 2); R, $R^1$, $R^2$, m, and n in Scheme 2 have the meanings as defined hereinbefore and hereinafter. The leaving group LG in IV is replaced with the NH group in III via a nucleophilic substitution reaction on the pyridine ring; suited LG may be F, Cl, Br, and I. The reaction is usually carried out in the presence of a base such as triethylamine, ethyldiisopropylamine, 1,8-diazabicyclo[5.4.0]undecene, carbonates, e.g., $Li_2CO_3$, $Na_2CO_3$, $K_2CO_3$, and $Cs_2CO_3$, hydroxides, e.g., LiOH, NaOH, and KOH, alcoholates, e.g., NaOMe, NaOEt, and KOtBu, and oxides, e.g., CaO and $Ag_2O$. Additives, such as silver salts, e.g., $AgNO_3$, $AgOSO_2CF_3$, and $Ag_2CO_3$, may be beneficial or essential for the reaction to proceed. Preferred solvents are dimethylsulfoxide, N,N-dimethylformamide, N,N-dimethylacetamide, N— methylpyrrolidinone, acetonitrile, 1,4-dioxane, tetrahydrofuran, toluene, alcohol, e.g., ethanol or isopropanol, water, or mixtures thereof at temperatures of 20 to 220° C. Alternatively, coupling of indanylamine III and compound IV is mediated by a transition metal catalyst. Suited compounds IV for this approach bear Cl, Br, or I as LG, and the catalyst is preferably derived from Cu, Ni, or Pd. The catalyst or the precursor thereof may be a complex of the transition metal with ligands such as phosphines, e.g., tri-tert-butylphosphine, tricyclohexylphosphine, optionally substituted biphenyl-dicyclohexyl-phosphines, optionally substituted biphenyl-di-tert-butylphosphines, Xantphos, 1,1'-bis(diphenylphosphino)ferrocene, triphenylphosphine, tritolylphosphine, or trifurylphosphine, phosphites, 1,3-disubstituted imidazole carbenes, 1,3-disubstituted imidazolidine carbenes, oxalamides, dibenzylideneacetone, allyl, or nitriles, an elemental form of the transition metal such as palladium on carbon or nanoparticles of palladium, or a salt of the transition metal such as fluoride, chloride, bromide, acetate, triflate, acetylacetonate, or trifluoroacetate that may be combined with a separately added ligand. The reaction is preferably conducted in the presence of a base such as an alcoholate, e.g., LiOtBu, NaOtBu, KOtBu, NaOtPent, and KOtPent, a hydroxide, e.g., LiOH, NaOH, and KOH, lithium hexamethyldisilazide, $K_3PO_4$, a carbonate such as $Cs_2CO_3$, or a phenolate such as sodium 2,6-di-tert-butyl-4-methyl-phenolate. Additives, such as silver salts, e.g., $AgNO_3$, $AgOSO_2CF_3$, and $Ag_2CO_3$, may be beneficial or essential for some of the reactions to proceed. The coupling reactions are preferably conducted in benzene, toluene, tetrahydrofuran, 1,2-dimethoxyethane, 1,4-dioxane, N,N-dimethylformamide, N,N-dimethylacetamide, N-methylpyrrolidinone, dimethyl sulfoxide, alcohol such as tBuOH or tPentOH, water, or mixtures thereof, at temperatures in the range of 20 to 180° C. For employing the chloro-compound IV as carboxylic acid ester (LG=Cl and CP=$COOCH_3$ or $COOCH_2CH_3$) particularly suited reaction conditions include chloro[2-(dicyclohexylphosphino)-3,6-dimethoxy-2',4',6'-triisopropyl-1,1'-biphenyl][2-(2-aminoethyl)phenyl]palladium(II) as catalyst precursor and sodium tert-butoxide or sodium tert-pentoxide as base, in 1,4-dioxane, toluene, tert-butanol, or tert-pentanol at 60 to 110° C.; optionally, an additional equivalent of 2-(dicyclohexylphosphino)-3,6-dimethoxy-2',4',6'-triisopropyl-1,1'-biphenyl is added.

Scheme 2: Preparation of precursor II

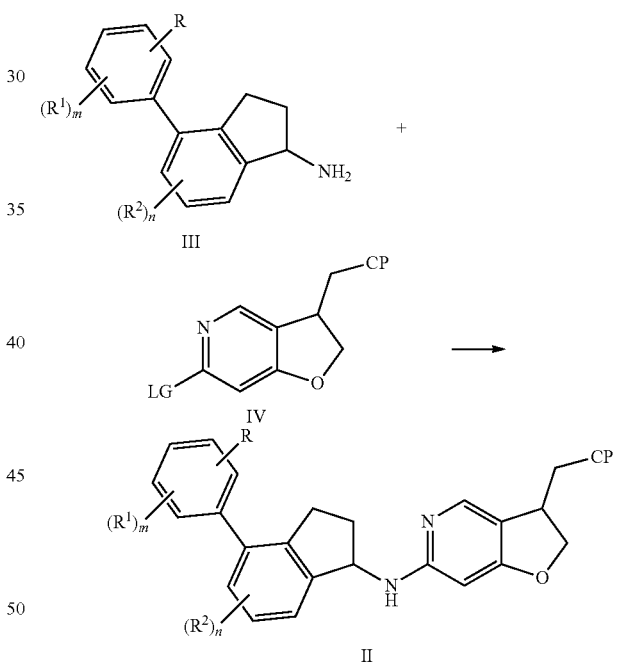

LG = leaving group, e.g., F, Cl, Br, I;
CP = COOH or masked or protected form of COOH, e.g., $CO_2C_{1-4}$-alkyl, $CO_2CH_2$aryl, $CON(C_{1-4}$-alkyl$)_2$, CN, CH=$CH_2$, thiazol-2-yl, oxazol-2-yl Intermediate III is conveniently obtained from indanol V which, in turn, may be prepared from indanone VI or VI' (Scheme 3); R, $R^1$, $R^2$, m and n in Scheme 3 have the meanings as defined hereinbefore and hereinafter.

The reduction of the keto group in compound VI or VI' is a standard transformation in organic synthesis which may be accomplished with lithium borohydride, sodium borohydride, lithium aluminum hydride, or diisobutylaluminum hydride. While sodium borohydride is commonly employed in aqueous or alcoholic solution at 0 to 60° C., the other reducing agents mentioned are preferably used in inert solvents, such as tetrahydrofuran, diethyl ether, dichloromethane, and toluene, at −80 to 60° C. The reduction of the keto group may also be conducted in a stereoselective fashion providing the alcohol in enantiomerically enriched or pure form. Suited chiral reducing agents are boranes combined with an enantiomerically pure [1,3,2]oxazaborol (Corey-Bakshi-Shibata reduction or Corey-Itsuno reduction) or formic acid, formates, hydrogen, or silanes in the presence of an enantiomerically pure transition metal catalyst. Typical reaction conditions for the former approach comprise a borane, e.g., borane dimethyl sulfide complex, and (R)- or (S)-3,3-diphenyl-1-methyltetrahydro-1H,3H-pyrrolo[1,2-c][1,3,2]oxazaborol in, e.g., dichloromethane, toluene, methanol, tetrahydrofuran, or mixtures thereof, at −10 to 60° C. Employing a chiral transition metal catalyst, such as a ruthenium complex, e.g., chloro{[(1S,2S)-(−)-2-amino-1,2-diphenylethyl](4-toluenesulfonyl)-amido}-(mesitylene)ruthenium(II), may deliver the hydroxy compound with high enantiomeric excess using a hydride source, e.g., formic acid, in the presence of a base, e.g., triethylamine, in dichloromethane, at −20 to 60° C. The OH group in compound V may be replaced with $NH_2$ following a two-step procedure via a protected, e.g., as phthalimide, or masked, e.g., as azide, amino derivative. Phthalimide can be introduced employing the conditions of the Mitsunobu reaction. The transformation is routinely conducted with phthalimide, a phosphine, and an azodicarboxylic ester or amide in tetrahydrofuran, 1,4-dioxane, diethyl ether, toluene, benzene, dichloromethane, or mixtures thereof, at −30 to 100° C. Phosphines commonly used are triphenylphosphine and tributylphosphine which are regularly combined with dimethyl azodicarboxylate, diethyl azodicarboxylate, diisopropyl azodicarboxylate, di-(4-chlorobenzyl) azodicarboxylate, dibenzyl azodicarboxylate, di-tert-butyl azodicarboxylate, azodicarboxylic acid bis-(dimethylamide), azodicarboxylic acid dipiperidide, or azodicarboxylic acid dimorpholide. The amino group may be liberated from phthalimide using hydrazine in ethanol, ethylene-1,2-diamine in n-butanol, or 1-butylamine in n-butanol.

The azide group can be introduced from the hydroxy precursors V and V' employing hydrazoic acid or phosphoryl azide and the conditions of the Mitsunobu reaction as described above or variants thereof. Phosphoryl azide combined with a base, such as 1,8-diazabicyclo[5.4.0]undecene, may also accomplish the transformation in tetrahydrofuran or toluene at −10 to 80° C. The azide is transformed into the amino function using, e.g., hydrogen in the presence of a transition metal such as palladium on carbon. Both proceedings may give the aminoindane III in enantiomerically pure form when starting from the isomerically pure precursor V or V'.

The phenyl residue on indane III is attached via a transition metal catalyzed coupling reaction that can be carried out at various stages of the synthesis sequence as depicted in Scheme 3 and described in the experimental section. The transition metal catalyst is preferably derived from palladium, nickel, copper, or iron, more preferably palladium. The active catalyst may be a complex of the transition metal with ligands such as phosphines, e.g. tri-tert-butylphosphine, tricyclohexylphosphine, optionally substituted biphenyl-dicyclohexyl-phosphines, optionally substituted biphenyl-di-tert-butyl-phosphines, 1,1'-bis(diphenylphosphino)-ferrocene, triphenylphosphine, tritolylphosphine, or trifurylphosphine, phosphites, 1,3-disubstituted imdiazole carbenes, 1,3-disubstituted imidazolidine carbenes, dibenzylideneacetone, allyl, or nitriles, an elemental form of the transition metal, such as palladium on carbon or nanoparticles of iron or palladium, or a salt such as fluoride, chloride, bromide, acetate, triflate, or trifluoroacetate. The phenyl group is preferably employed as boronic acid or ester, trifluoroborate, or zinc halide, the nucleophilic reaction partner (VI''), and the indane derivative as chloride, bromide or iodide, the electrophilic reaction partner (III', V', or VI''). Depending on the nucleophiles the reactions are preferably conducted in benzene, toluene, ether, tetrahydrofuran, 1,2-dimethoxyethane, 1,4-dioxane, N,N-dimethylformamide, N,N-dimethylacetamide, N-methylpyrrolidinone, dimethylsulfoxide, alcohol, water, or mixtures thereof, at 0 to 160° C. Reactions employing boronic acids or esters or trifluoroborates are commonly conducted in the presence of a base such as an alcoholate, a hydroxide, e.g., LiOH, NaOH, and KOH, $K_3PO_4$, a carbonate, e.g., $Li_2CO_3$, $Na_2CO_3$, $K_2CO_3$, and $Cs_2CO_3$, an amine, or a fluoride, e.g., KF. Additives such as halide salts, e.g., lithium chloride, silver salts, e.g., silver oxide and triflate, and/or copper salts, e.g., copper chloride and copper thiophene-2-carboxylate, may be beneficial or even essential for the reaction to proceed. The reactivities of the reaction partners (reacting carbons) described may be reversed, i.e. the phenyl derivative is the electrophilic and the indanyl derivative the nucleophilic reaction partner, providing the same products under the same or similar conditions.

Scheme 3: Preparation of intermediate III

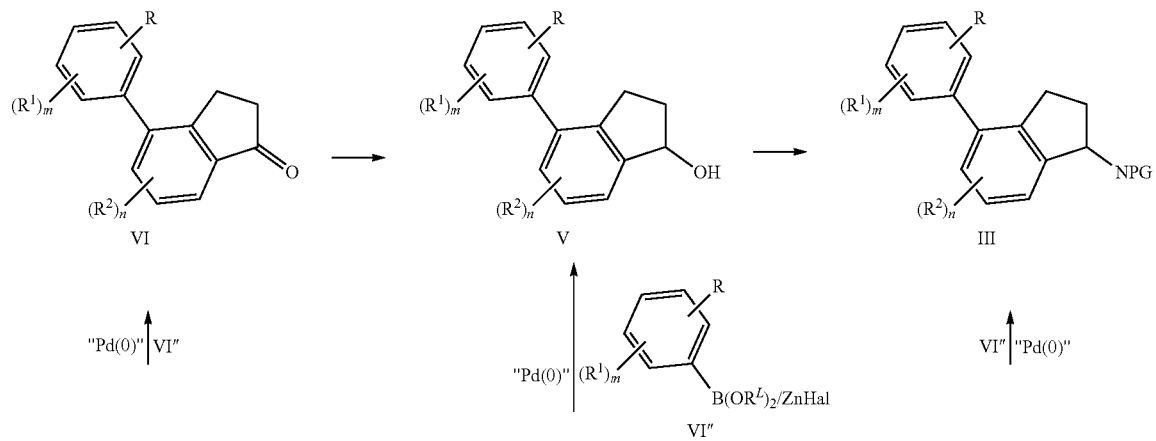

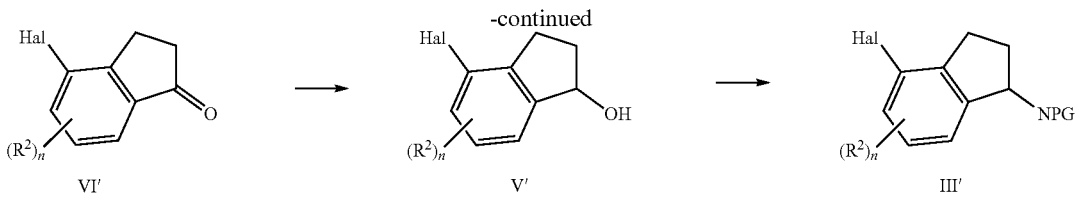

Hal = Cl, Br, I; B(OR$^L$)$_2$ = B(OH)$_2$, B(OCMe$_2$CMe$_2$O)
NPG = NH$_2$ or protected or masked NH$_2$ such as N$_3$, phthalimide or NHCOOtBu Compounds of general structure IV may be synthesized as described in the experimental section and summarized in Scheme 4. Starting from pyridine VII pyridine VIII may be obtained upon treatment with an excess of an iodine electrophile such as N-iodosuccinimide (NIS). Monoreduction of pyridine VIII may be accomplished via a selective iodine-metal exchange reaction employing an alkyl metal compound such as a Grignard reagent, e.g., $^i$PrMgCl, and protonolysis of the resulting pyridyl-metal compound. Alkylation of pyridinol IX with a bromo-crotonate (e.g., X) in the presence of a base furnishes the cyclization precursor XI. Compound XI may be transformed into compound IV' via radical cyclization upon generation of a carbon radical from the C-I unit and hydrogen interception of the cyclized radical species with, e.g., tris(trimethylsilyl)silane or tri-n-butyl-stannane and a radical initiator.

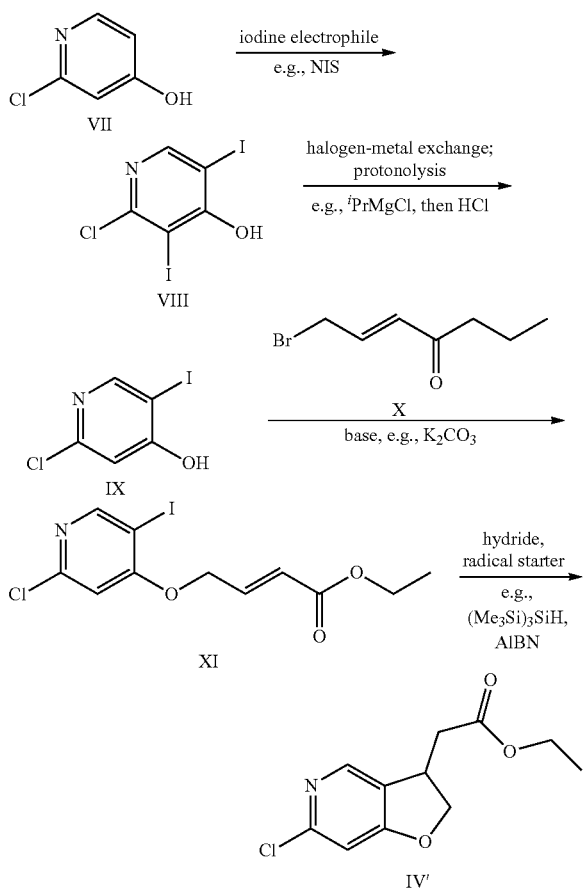

Scheme 4: Preparation of intermediate IV

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis for example in "Protecting Groups", 3$^{rd}$ Edition, Philip J. Kocienski, Thieme, 2005, and "Protective Groups in Organic Synthesis", 4$^{th}$ Edition, Peter G. M. Wuts, Theodora W. Greene, John Wiley & Sons, 2006.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the G-protein-coupled receptor GPR40 with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

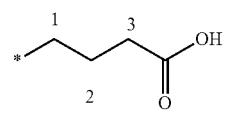 [SMILES: *CCCC(=O)O]

wherein the carboxy group is attached to the third carbon atom of the propyl group. The terms "1-methylpropyl-", "2,2-dimethylpropyl-" or "cyclopropylmethyl-" group represent the following groups:

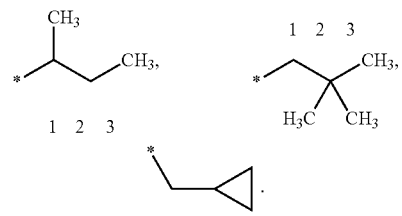

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$ and $H_3C—CH_2—CH(CH_2CH_3)—$.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes $—(CH_2)—$, $—(CH_2—CH_2)—$, $—(CH(CH_3))—$, $—(CH_2—CH_2—CH_2)—$, $—(C(CH_3)_2)—$, $—(CH(CH_2CH_3))—$, $—(CH(CH_3)—CH_2)—$, $—(CH_2—CH(CH_3))—$, $—(CH_2—CH_2—CH_2—CH_2)—$, $—(CH_2—CH_2—CH(CH_3))—$, $—(CH(CH_3)—CH_2—CH_2)—$, $—(CH_2—CH(CH_3)—CH_2)—$, $—(CH_2—C(CH_3)_2)—$, $—(C(CH_3)_2—CH_2)—$, $—(CH(CH_3)—CH(CH_3))—$, $—(CH_2—CH(CH_2CH_3))—$, $—(CH(CH_2CH_3)—CH_2)—$, $—(CH(CH_2CH_2CH_3))—$, $—(CHCH(CH_3)_2)—$ and $—C(CH_3)(CH_2CH_3)—$.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes $—CH=CH_2$, $—CH=CH—CH_3$, $—CH_2—CH=CH_2$.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes $—C≡CH$, $—C≡C—CH_3$, $—CH_2—C≡CH$.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclo-pentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

Many of the terms given above may be used repeatedly in the definition of a formula or group and in each case have one of the meanings given above, independently of one another.

Pharmacological Activity

The activity of the compounds of the invention may be demonstrated using the following assay:

IP1 accumulation measurements using the IPOne assay system—1321N1 cells stably expressing human GPR40 receptor (Euroscreen, Belgium) are seeded 24 h before the assay in white 384-well plates in culture medium containing 10% FCS, 1% Na-Pyruvate and 400 µg/mL G418. IP1 is assayed according to the manufacturer's description (Cisbio Bioassays, France). In brief, the assay is started by substitution of the culture medium by stimulation buffer (Hepes 10 mM, $CaCl_2$) 1 mM, $MgCl_2$ 0.5 mM, KCl 4.2 mM, NaCl 146 mM, glucose 5.5 mM and LiCl 50 mM, pH 7.4). Cells are stimulated for 1 h at 37° C., 5% $CO_2$ by addition of the compounds that are diluted in stimulation buffer containing LiCl. Assays are stopped by adding HTRF-conjugates (IP1-d2 and Anti-IP1 cryptate Tb) and lysis buffer, provided by the manufacturer. After an incubation time of 1 h at room temperature plates are measured using an EnVision™, Perkin Elmer. The obtained fluorescence ratios at 665/615 nM are then used to calculate the $pEC_{50}$ values using Assay Explorer 3.3 Software (Accelrys, Inc.) by interpolation using an IP1 reference curve and subsequent sigmoidal curve fitting allowing for a variable hill slope.

The compounds according to the invention typically have $EC_{50}$ values in the range from about 1 nM to about 10 µM, preferably less than 1 µM, more preferably less than 100 nM.

$EC_{50}$ values for compounds according to the invention are shown in the following table. The number of the compound corresponds to the number of the Example in the experimental section.

TABLE 2

| Example | $EC_{50}$ [nM] | Example | $EC_{50}$ [nM] | Example | $EC_{50}$ [nM] | Example | $EC_{50}$ [nM] |
|---|---|---|---|---|---|---|---|
| 1 | 15 | 2 | 764 | 3 | 21 | 4 | 751 |
| 5 | 6 | 6 | 382 | 7 | 7 | 8 | 378 |
| 9 | 57 | 10 | 56 | 11 | 37 | 12 | 73 |
| 13 | 35 | 14 | 27 | 15 | 9 | 16 | 27 |
| 17 | 12 | 18 | 14 | 19 | 27 | 20 | 9 |

Solubility

The aqueous solubility of the compounds of the invention is determined by comparing the amount dissolved in buffer to the amount in an acetonitrile/water (1/1) solution. Starting from a 10 mM DMSO stock solution aliquots are diluted with acetonitrile/water (1/1) or buffer, respectively. After 24 h of shaking, the solutions are filtrated and analyzed by LC-UV. The amount dissolved in buffer is compared to the amount in the acetonitrile solution.

Solubility is usually being measured from 0.001 to 0.125 mg/mL at a DMSO concentration of 2.5%. If more than 90% of the compound is dissolved in buffer, the value is marked with ">".

The compounds of the invention show higher solubility at low pH value (pH 2.2) compared with their direct structural counterparts explicitly disclosed in WO 2013/144098. Their development and application is therefore more convenient and reliable. The compilation below the section "Inhibiton of CYP-2C9" presents the data for selected compounds of this invention and their direct structural counterparts from WO 2013/144098.

Inhibition of CYP-2C8

The inhibition of cytochrome P450 2C8-isoenzyme catalyzed deethylation of amodiaquine by the test compound is assayed at 37° C. with human liver microsomes. All assays are carried out on a robotic system in 96 well plates. The final incubation volume contains TRIS buffer (0.1 M), $MgCl_2$ (5 mM), human liver microsomes (0.05 mg/mL), amodiaquine (1 µM) and the test compound at five different concentrations or no compound (high control) in duplicate (e.g. highest concentration 10-50 µM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—the stable isotope d5-desethyl-amodiaquine—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the $IC_{50}$ of a positive control inhibitor (Montelukast) is determined. Experimental $IC_{50}$ values are calculated by least square regression according to the following equation:

% control activity=(100% control activity/(1+($I/IC_{50}$) $S$))−$B$ with I=inhibitor concentration; S=slope factor; B=background activity (lower plateau of the inhibition curve)

If the inhibition of the reaction is already >50% at the lowest concentration of the test compound, the $IC_{50}$ is assigned "<lowest concentration tested" (usually <0.4 µM). If the inhibition of the reaction is still <50% at the highest concentration of the test compound, the $IC_{50}$ is assigned "> highest concentration tested" (usually >50 µM).

The compounds of the invention show lower inhibition of the cytochrome P450 2C8-isoenzyme compared with their direct structural counterparts explicitly disclosed in WO 2013/144098. Their potential for causing unwanted side-effects is therefore decreased. The compilation below the section "Inhibiton of CYP-2C9" displays the data for selected compounds of this invention and their direct structural counterparts from WO 2013/144098.

Inhibition of CYP-2C9

The inhibition of cytochrome P450 2C9-isoenzyme catalyzed hydroxylation of diclofenac by the test compound is assayed at 37° C. with human liver microsomes. All assays are carried out on a robotic system in 96 well plates. The final incubation volume contains TRIS buffer (0.1 M), $MgCl_2$ (5 mM), human liver microsomes (0.1 mg/mL), diclofenac (10 µM) and the test compound at five different concentrations or no compound (high control) in duplicate (e.g., highest concentration 10-50 µM with subsequent serial 1:4 dilutions). Following a short preincubation period, reactions are started with the cofactor (NADPH, 1 mM) and stopped by cooling the incubation down to 8° C. and subsequently by addition of one volume of acetonitrile. An internal standard solution—the stable isotope $^{13}C6$-hydroxydiclofenac—is added after quenching of incubations. Peak area analyte (=metabolite formed) and internal standard is determined by LC-MS/MS. The resulting peak area ratio analyte to internal standard in these incubations is compared to a control activity containing no test compound. Within each of the assay runs, the $IC_{50}$ of a positive control inhibitor (sulfaphenazole) is determined. Experimental $IC_{50}$ values are calculated by least square regression according to the following equation:

% control activity=(100% control activity/(1+($I/IC_{50}$) $S$))−$B$ with I=inhibitor concentration; S=slope factor; B=background activity (lower plateau of the inhibition curve)

If the inhibition of the reaction is already >50% at the lowest concentration of the test compound, the $IC_{50}$ is assigned "<lowest concentration tested" (usually <0.4 µM). If the inhibition of the reaction is still <50% at the highest concentration of the test compound, the $IC_{50}$ is assigned "> highest concentration tested" (usually >50 µM).

The compounds of the invention show lower inhibition of the cytochrome P450 2C9-isoenzyme compared with their structural counterparts explicitly disclosed in WO 2013/144098. Their potential for causing unwanted side-effects is therefore decreased.

The compilation below presents the data for selected compounds of this invention and their direct structural counterparts from WO 2013/144098.

The following compilation showcases the superiority of selected compounds of this invention over the compounds from WO 2013/144098 with regard to solubility, inhibition of CYP-2C8, and inhibition of CYP-2C9 by head-to-head comparison of their direct structural analogs.

| Example 1 in this invention | Example 16 in WO 2013/144098 |
|---|---|
| 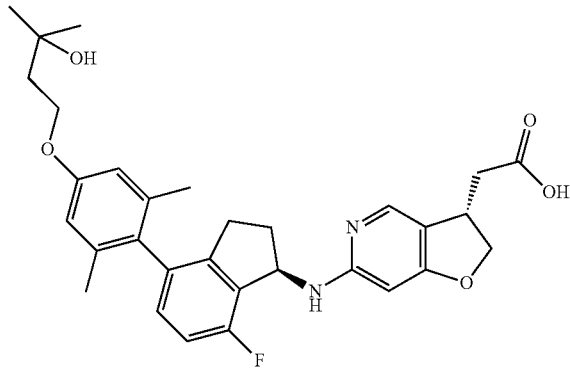 [SMILES: Cc1cc(OCCC(C)(C)O)cc(C)c1-c1ccc(F)c2c1CC[C@H]2Nc1cc2c(cn1)[C@H](CC(=O)O)CO2] | 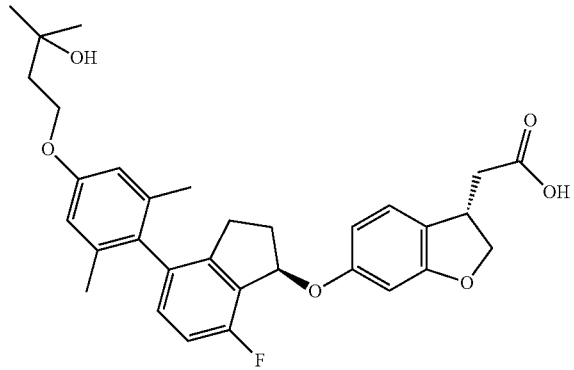 [SMILES: Cc1cc(OCCC(C)(C)O)cc(C)c1-c1ccc(F)c2c1CC[C@H]2Oc1ccc2c(c1)OC[C@H]2CC(=O)O] |
| Solubility (pH 2.2) >94 µg/mL<br>Cyp 2C8: $IC_{50}$ = 30<br>Cyp 2C9: $IC_{50}$ >50 µM | <1 µg/mL<br>$IC_{50}$ = 5 µM<br>$IC_{50}$ = 21 µM |

| Example 5 in this invention | Example 138 in WO 2013/144098 |
|---|---|
| 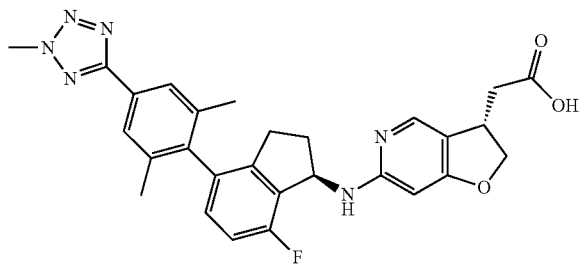 [SMILES: Cc1cc(-c2nnn(C)n2)cc(C)c1-c1ccc(F)c2c1CC[C@H]2Nc1cc2c(cn1)[C@H](CC(=O)O)CO2] | 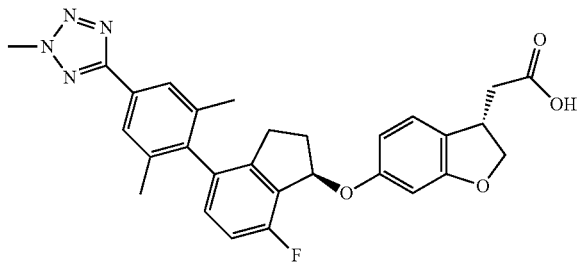 [SMILES: Cc1cc(-c2nnn(C)n2)cc(C)c1-c1ccc(F)c2c1CC[C@H]2Oc1ccc2c(c1)OC[C@H]2CC(=O)O] |
| Solubility (pH 2.2) = 47 μg/mL<br>Cyp 2C8: $IC_{50}$ = 35 μM<br>Cyp 2C9: $IC_{50}$ >50 μM | <1 μg/mL<br>$IC_{50}$ = 9 μM<br>$IC_{50}$ = 19 μM |

In view of their ability to modulate the activity of the G-protein-coupled receptor GPR40, in particular an agonistic activity, the compounds of general formula I according to the invention, including the corresponding salts thereof, are theoretically suitable for the treatment of all those diseases or conditions which may be affected or which are mediated by the activation of the G-protein-coupled receptor GPR40.

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the G-protein-coupled receptor GPR40 in a patient, preferably in a human.

In yet another aspect the present invention relates to a method for treating a disease or condition mediated by the activation of the G-protein-coupled receptor GPR40 in a mammal that includes the step of administering to a patient, preferably a human, in need of such treatment a therapeutically effective amount of a compound or a pharmaceutical composition of the present invention.

Diseases and conditions mediated by agonists of the G-protein-coupled receptor GPR40 embrace metabolic diseases or conditions. According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable.

Angiotensin II receptor antagonists are preferably used for the treatment or prevention of high blood pressure and complications of diabetes, often combined with a diuretic such as hydrochlorothiazide.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the G-protein-coupled receptor GPR40, in particular diseases or conditions as described hereinbefore and hereinafter.

In yet another aspect the present invention relates a method for treating a disease or condition mediated by the activation of the G-protein-coupled receptor GPR40 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

The terms "ambient temperature" and "room temperature" are used interchangeably and designate a temperature of about 20° C.

As a rule, $^1$H-NMR and/or mass spectra have been obtained for the compounds prepared.

Intermediates and Examples reported in the following bearing a basic or acidic group may be obtained as a corresponding salt or neutral compound depending on the purification method and conditions employed. Salts can be transformed into their neutral counterparts by standard procedures known to the one skilled in the art.

Analytical HPLC parameters employed for characterization of products (TFA denotes trifluoroacetic acid):

| Method: | 1 |
| --- | --- |
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% TFA] | % Solvent [Acetonitrile] | Flow [mL/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

| Method: | 2 |
| --- | --- |
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% HCO$_2$H] | % Solvent [Acetonitrile] | Flow [mL/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

| Method: | 3 |
| --- | --- |
| Device: | Waters Acquity, QDa Detector |
| Column: | XBridge C18, 3 × 30 mm, 2.5 μm |
| Column Supplier: | Waters |

| Gradient/ Solvent Time [min] | % Solvent [H$_2$O, 0.1% NH$_3$] | % Solvent [Acetonitrile] | Flow [mL/min] | Temperature [° C.] |
| --- | --- | --- | --- | --- |
| 0.0 | 95 | 5 | 1.5 | 40 |
| 1.3 | 0 | 100 | 1.5 | 40 |
| 1.5 | 0 | 100 | 1.5 | 40 |
| 1.6 | 95 | 5 | 1.5 | 40 |

| Method: | 4 |
| --- | --- |
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% NH$_4$OH] | % Solvent [Acetonitrile] | Flow [mL/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

The Examples that follow are intended to illustrate the present invention without restricting it:

Intermediate 1

(6-Chloro-2,3-dihydro-furo[3,2-c]pyridin-3-yl)-acetic acid ethyl ester

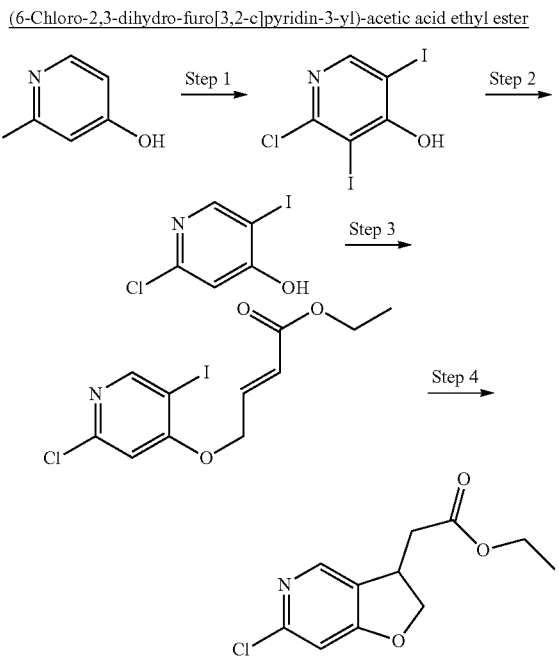

Step 1: 2-Chloro-3,5-diiodopyridin-4-ol

N-iodosuccinimide (23.3 g) is added to a solution of 2-chloro-pyridin-4-ol (7.0 g) in water (150 mL) chilled in an ice bath. The mixture is stirred at room temperature for 1 h. The precipitate is filtered off and dried in vacuo to give the title compound. Mass spectrum (ESI$^+$): m/z=382/384 (Cl) [M+H]$^+$.

Step 2: 2-Chloro-5-iodopyridin-4-ol $^i$Pr—MgCl (36.8 mL, 2 mol/L in tetrahydrofuran) is added dropwise to a flask charged with a stir bar, 2-chloro- 3,5-diiodopyridin-4-ol (10 g), and tetrahydrofuran (150 mL) cooled to −78° C. The mixture is stirred at −78° C. for 1 h and at −20° C. for 12 h. Hydrochloric acid (18.8 mL, 4 M in water) in 1,4-dioxane (70 mL) is added dropwise at 0° C. The precipitate is filtered off, and the filtrate is concentrated to give the title compound. Mass spectrum (ESI$^+$): m/z=256/258 (Cl) [M+H]$^+$.

Step 3: (E)-4-(2-Chloro-5-iodo-pyridin-4-yloxy)-but-2-enoic acid ethyl ester

Ethyl 4-bromo-crotonate (14.2 mL) is added dropwise to a flask charged with a stir bar, 2-chloro-5-iodopyridin-4-ol (9.9 g), $K_2CO_3$ (21.3 g), and N,N-dimethylformamide (100 mL) chilled in an ice bath. The ice bath is removed, and the mixture is stirred at room temperature 2 h. Water is added, and the resulting mixture is extracted with methyl-tert-butyl-ether. The combined organic phases are washed with water and brine, dried ($MgSO_4$), and concentrated. The residue is chromatographed on silica gel (cyclohexane/ethyl acetate 70:30-20:80) to give the title compound. Mass spectrum (ESI$^+$): m/z=368/370 (Cl) [M+H]$^+$.

Step 4: (6-Chloro-2,3-dihydro-furo[3,2-c]pyridin-3-yl)-acetic Acid Ethyl Ester

A mixture of (E)-4-(2-chloro-5-iodo-pyridin-4-yloxy)-but-2-enoic acid ethyl ester (5.8 g), tris-(trimethylsilyl)-silane (20 mL), azo-bis-isobutyronitrile (AIBN; 1.3 g), and toluene (20 mL) is stirred 90° C. for 30 min. The solvent are evaporated, and the residue is chromatographed on silica gel (cyclohexane/methyl-tert-butylether 90:10-0:100) to give the title compound. $R_f$ value (ethyl acetate/petrol ether 1:4): 0.45; LC (method 1): $t_R$=0.89 min; Mass spectrum (ESI$^+$): m/z=242/244 (Cl) [M+H]$^+$.

The title compound is resolved into its enantiomers by HPLC on chiral phase (Column: Chiralpak AD-H, 250×30 mm; Solvent: $CO_2$/methanol 60:40; Flow: 100.0 g/min; Temp.: 25° C.):

Intermediate 1a ((S)-6-Chloro-2,3-dihydro-furo[3,2-c]pyridin-3-yl)-acetic Acid Ethyl Ester

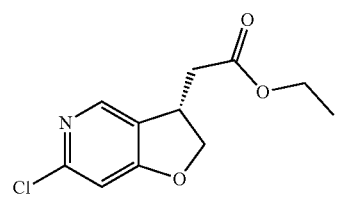 [SMILES: CCOC(=O)C[C@@H]1COc2cc(Cl)ncc21]

HPLC on reversed phase (Column: Chiralpak IB, 250×4.6 mm, 5 μm; Solvent: hexane/ethanol 85:15; Flow: 1.0 ml/min; Temp.: 25° C.): $t_R$=6.70 min;

Mass spectrum (ES$^+$): m/z=242/244 (Cl) [M+H]$^+$;

the configuration of the stereogenic C center is assigned based on data for analogous compounds described in the literature.

Intermediate 1b ((R)-6-Chloro-2,3-dihydro-furo[3,2-c]pyridin-3-yl)-acetic Acid Ethyl Ester

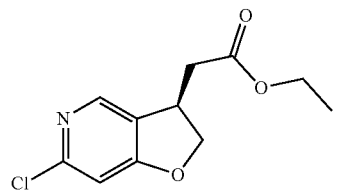 [SMILES: CCOC(=O)C[C@H]1COc2cc(Cl)ncc21]

HPLC on reversed phase (Column: Chiralpak IB, 250×4.6 mm, 5 μm; Solvent: hexane/ethanol 85:15; Flow: 1.0 ml/min; Temp.: 25° C.): $t_R$=7.12 min;

Mass spectrum (ES$^+$): m/z=242/244 (Cl) [M+H]$^+$;

the configuration of the stereogenic C center is assigned based on data for analogous compounds described in the literature.

Intermediate 2

4-[4-((R)-1-Amino-7-fluoro-indan-4-yl)-3,5-dimethyl-phenoxy]-2-methyl-butan-2-ol

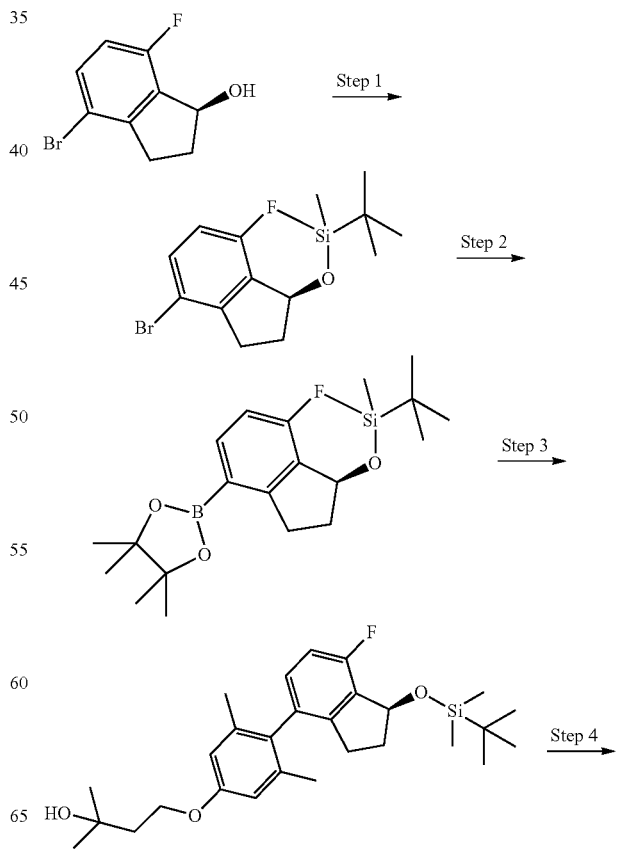

-continued

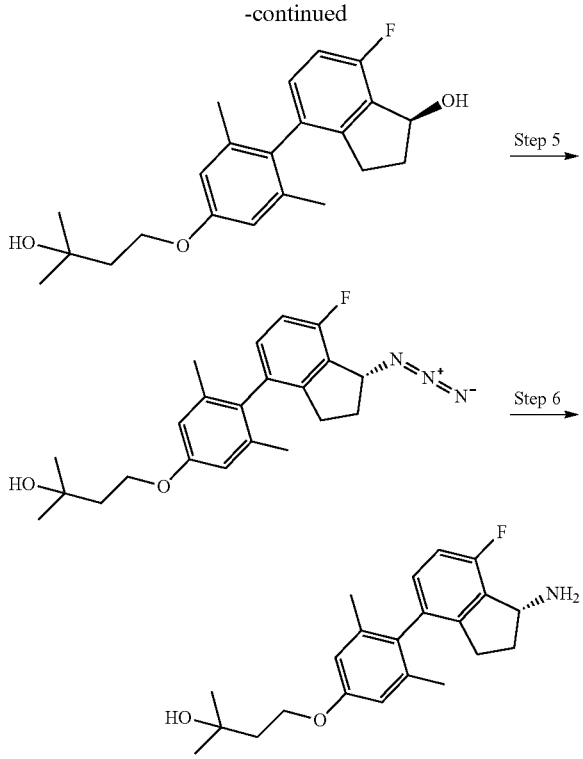

Step 1: ((S)-4-Bromo-7-fluoro-indan-1-yloxy)-tert-butyl-dimethyl-silane

Imidazole (4.5 g) and tert-butyl-dimethyl-chlorosilane (5.3 g) are added to a solution of (S)-4-bromo-7-fluoro-indan-1-ol (7.0 g) in N,N-dimethylformamide (30 mL) at 0° C. The mixture is stirred at room temperature for 12 h. Water is added, and the mixture is stirred for 10 min. Hydrochloric acid (1 mol/L in water) is added, and the resulting mixture is extracted with diethyl ether. The combined organic phases are washed with brine and dried (MgSO₄). The solvent is evaporated, and the residue is chromatographed on silica gel (cyclohexane/ethyl acetate 97:3→80:20) to give the title compound. Mass spectrum (ESI⁺): m/z=345/347 (Br) [M+H]⁺.

Step 2: 2-[(S)-1-(tert-Butyl-dimethyl-silanyloxy)-7-fluoro-indan-4-yl]-4,4,5,5-tetramethyl-[1,3,2]dioxaborolane A flask charged with a stir bar, ((S)-4-bromo-7-fluoro-indan-1-yloxy)-tert-butyl-dimethyl-silane (10.1 g), bis-(pinacolato)-diboron (9.9 g), potassium acetate (7.2 g), and 1,4-dioxane (50 mL) is purged with argon for 10 min. [1,1'-Bis(diphenylphosphino)-ferrocene]-dichloropalladium (II) (0.64 g) is added, and the mixture is stirred at 100° C. for 6 h. After cooling to room temperature, saturated aqueous NH₄Cl solution is added, and the resulting the mixture is extracted with diethyl ether. The combined organic phase is dried (MgSO₄) and concentrated. The residue is chromatographed on silica gel (cyclohexane/ethyl acetate 95:5-60:40) to give the title compound. Mass spectrum (ESI⁺): m/z=415 [M+Na]⁺.

Step 3: 4-{4-[(S)-1-(tert-Butyl-dimethyl-silanyloxy)-7-fluoro-indan-4-yl]-3,5-dimethyl-phenoxy}-2-methyl-butan-2-ol A vial charged with a stir bar, 2-[(S)-1-(tert-butyl-dimethyl-silanyloxy)-7-fluoro-indan-4-yl]-4,4,5,5-tetramethyl-[1,3,2]dioxaborolane (2.0 g), 4-(4-bromo-3,5-dimethylphenoxy)-2-methylbutan-2-ol (1.6 g), K₃PO₄ (3.3 g), 1,4-dioxane (20 mL), and water (3 mL) is purged with argon for. Palladium(II)acetate (35 mg) and dicyclohexyl(2',6'-dimethoxybiphenyl-2-yl)phosphine (S-Phos) (130 mg) are added, the vial is sealed, and the mixture is stirred at 80° C. for 2 h. After cooling to room temperature, the mixture is filtered over celite. The filtrate is concentrated, and the residue is chromatographed on silica gel (cyclohexane/ethyl acetate 60:40) to give the title compound. Mass spectrum (ESI⁺): m/z=455 [M+H−H₂O]⁺.

Step 4: (S)-7-Fluoro-4-[4-(3-hydroxy-3-methyl-butoxy)-2,6-dimethyl-phenyl]-indan-1-ol Tetrabutylammonium fluoride (7.6 mL, 1 mol/L in tetrahydrofuran) is added to a flask charged with a stir bar, 4-{4-[(S)-1-(tert-butyl-dimethyl-silanyloxy)-7-fluoro-indan-4-yl]-3,5-dimethyl-phenoxy}-2-methyl-butan-2-ol (2.2 g), and tetrahydrofuran (30 mL) at room temperature. The mixture is stirred for 3 h. Water is added, and the resulting mixture is extracted with ethyl acetate. The combined organic extracts are washed with brine, dried (MgSO₄), and concentrated. The residue is chromatographed on silica gel (cyclohexane/ethyl acetate 60:40-0:100) to give the title compound. Mass spectrum (ES⁺): m/z=376 [M+NH₄]⁺.

Step 5: 4-[4-((R)-1-Azido-7-fluoro-indan-4-yl)-3,5-dimethyl-phenoxy]-2-methyl-butan-2-ol A solution of 1,8-diazabicyclo[5.4.0]undec-7-ene (DBU, 0.9 mL) in toluene (8 mL) is added dropwise to a flask charged with a stir bar, (S)-7-fluoro-4-[4-(3-hydroxy-3-methyl-butoxy)-2,6-dimethyl-phenyl]-indan-1-ol (1.5 g), diphenylphosphorylazide (1.1 mL), and toluene (12 mL) cooled to 0° C. The mixture is stirred at 10° C. for 2 h. Water is added, and the resulting mixture is extracted with ethyl acetate. The combined organic extracts are washed with brine, dried (MgSO₄), and concentrated. The residue is chromatographed on silica gel (cyclohexane/ethyl acetate 60:40-40:60) to give the title compound. Mass spectrum (ESI⁺): m/z=366 [M+H−H₂O]⁺.

Step 6: 4-[4-((R)-1-Amino-7-fluoro-indan-4-yl)-3,5-dimethyl-phenoxy]-2-methyl-butan-2-ol A mixture of 10% Palladium on carbon (100 mg), 4-[4-((R)-1-azido-7-fluoro-indan-4-yl)-3,5-dimethyl-phenoxy]-2-methyl-butan-2-ol (1.2 g), and ethanol (20 mL) is shaken under hydrogen atmosphere (2 bar) at room temperature for 1 h. The catalyst is filtered off and washed with ethanol. The combined filtrate is concentrated, and the residue is chromatographed on silica gel (CH₂Cl₂/(CH₂Cl₂/methanol/7 N aqueous NH₄OH 50:48:2) 90:10→10:90) to give the title compound. Mass spectrum (ESI⁺): m/z=358 [M+H]⁺.

Intermediate 3

4-[4-((R)-1-Amino-indan-4-yl)-3,5-dimethyl-phenoxy]-2-methyl-butan-2-ol

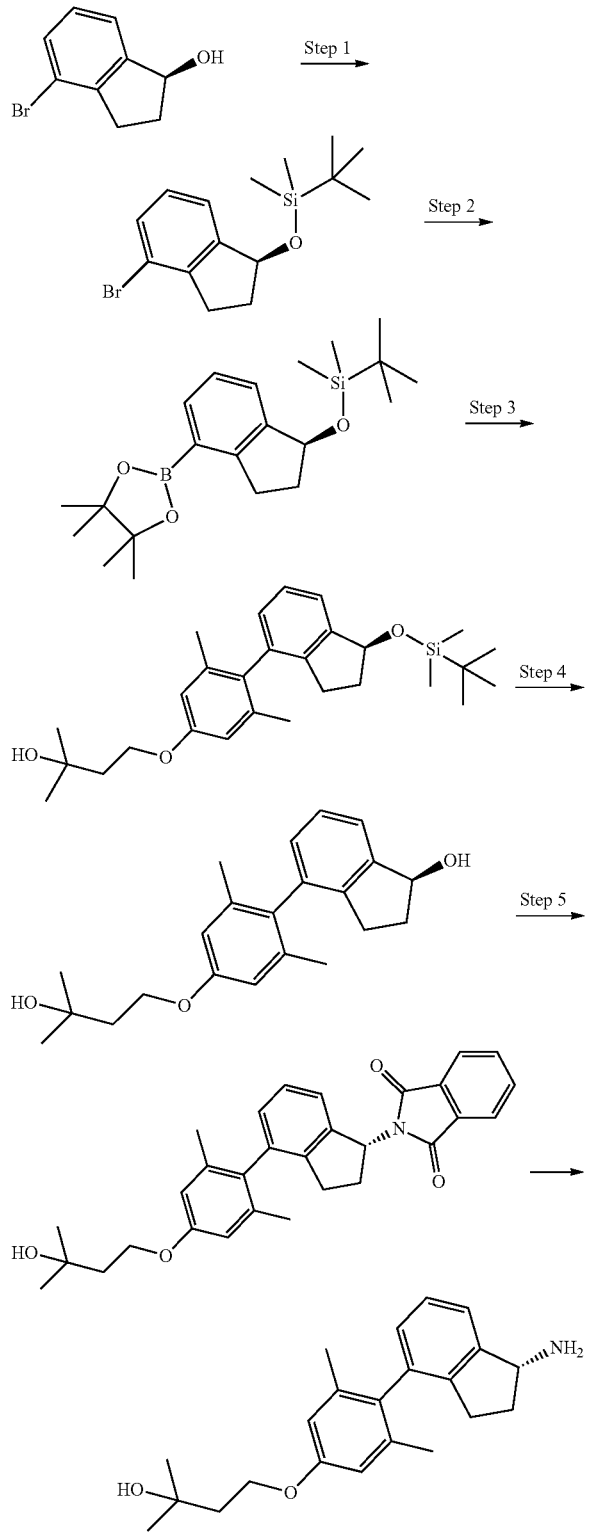

Step 1: ((S)-4-Bromo-indan-1-yloxy)-tert-butyl-dimethyl-silane

The title compound is prepared from (S)-4-bromo-indan-1-ol following a procedure analogous to that described in Step 1 of Intermediate 2.

Step 2: 2-[(S)-1-(tert-Butyl-dimethyl-silanyloxy)-indan-4-yl]-4,4,5,5-tetramethyl-[1,3,2]dioxaborolane The title compound is prepared from ((S)-4-bromo-indan-1-yloxy)-tert-butyl-dimethyl-silane following a procedure analogous to that described in Step 2 of Intermediate 2. Mass spectrum (ESI$^+$): m/z=397 [M+Na]$^+$.

Step 3: 4-{4-[(S)-1-(tert-Butyl-dimethyl-silanyloxy)-indan-4-yl]-3,5-dimethyl-phenoxy}-2-methyl-butan-2-ol The title compound is prepared from 2-[(S)-1-(tert-butyl-dimethyl-silanyloxy)-indan-4-yl]-4,4,5,5-tetramethyl-[1,3,2]dioxaborolane following a procedure analogous to that described in Step 3 of Intermediate 2. Mass spectrum (ESI$^+$): m/z=477 [M+Na]$^+$.

Step 4: (S)-4-[4-(3-Hydroxy-3-methyl-butoxy)-2,6-dimethyl-phenyl]-indan-1-ol The title compound is prepared from 4-{4-[(S)-1-(tert-Butyl-dimethyl-silanyloxy)-indan-4-yl]-3,5-dimethyl-phenoxy}-2-methyl-butan-2-ol following a procedure analogous to that described in Step 4 of Intermediate 2. Mass spectrum (ESI$^+$): m/z=363 [M+Na]$^+$.

Step 5: 2-{(R)-4-[4-(3-Hydroxy-3-methyl-butoxy)-2,6-dimethyl-phenyl]-indan-1-yl}-isoindole-1,3-dione Di-tert-butyl azodicarboxylate (0.71 g) is added portionwise to flask charged with a stir bar, (S)-4-[4-(3-hydroxy-3-methyl-butoxy)-2,6-dimethyl-phenyl]-indan-1-ol (1.0 g), phthalimide (0.45 g), triphenylphosphine (0.81 g), and tetrahydrofuran (20 mL) at 0° C. The resulting mixture is stirred at room temperature for 4 h. The mixture is concentrated, and the residue is chromatographed on silica gel (cyclohexane/ethyl acetate 80:20→40:60) to give the title compound. Mass spectrum (ESI$^+$): m/z=452 [M+H−H$_2$O]$^+$.

Step 6: 4-[4-((R)-1-Amino-indan-4-yl)-3,5-dimethyl-phenoxy]-2-methyl-butan-2-ol Hydrazine hydrate (3.0 mL) is added to a solution of 2-{(R)-4-[4-(3-hydroxy-3-methyl-butoxy)-2,6-dimethyl-phenyl]-indan-1-yl}-isoindole-1,3-dione (0.65 g) in methanol (25 mL) at room temperature. The mixture is stirred for 5 h and then concentrated. The residue is chromatographed on silica gel (CH$_2$Cl$_2$/(CH$_2$Cl$_2$/methanol/7 N aqueous NH$_4$OH 50:48:2) 90:10→60:40) to give the title compound. Mass spectrum (ESI$^+$): m/z=323 [M+H−H$_2$O]$^+$.

Intermediate 4

(R)-4-[2,6-Dimethyl-4-(2-methyl-2H-tetrazol-5-yl)-phenyl]-7-fluoro-indan-1-ylamine

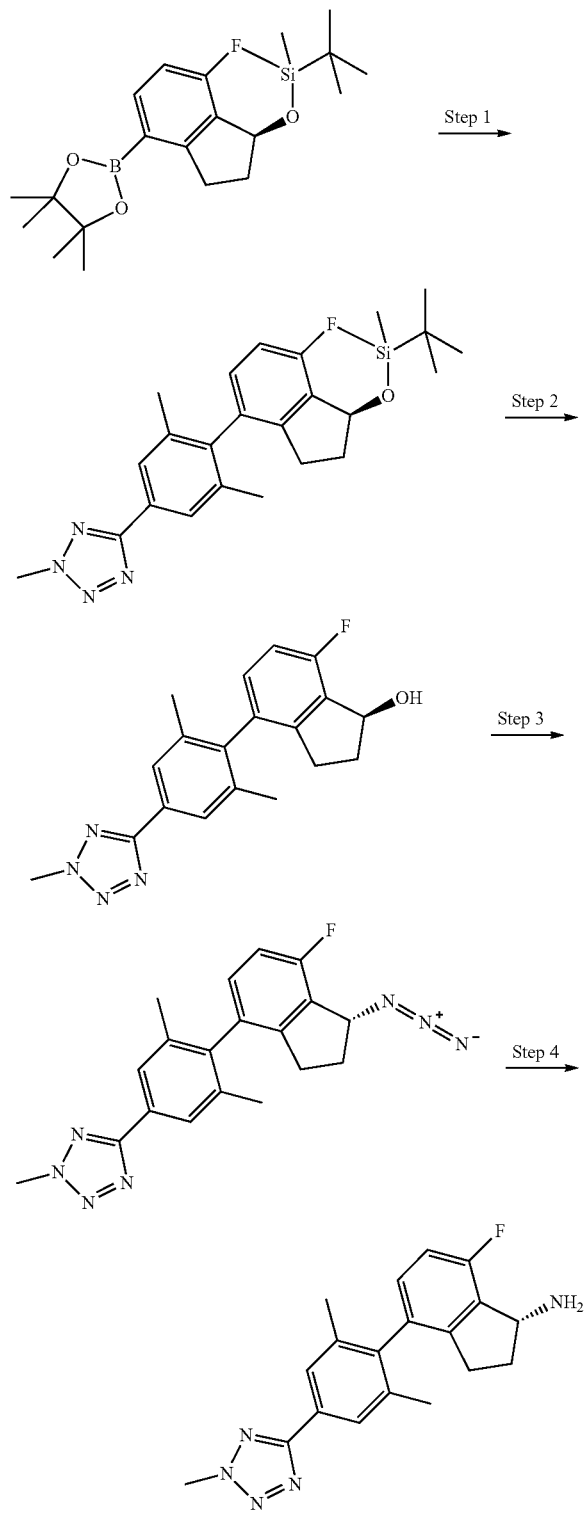

Step 1: 5-{4-[(S)-1-(tert-Butyl-dimethyl-silanyloxy)-7-fluoro-indan-4-yl]-3,5-dimethyl-phenyl}-2-methyl-2H-tetrazole The title compound is prepared from 2-[(S)-1-(tert-butyl-dimethyl-silanyloxy)-7-fluoro-indan-4-yl]-4,4,5,5-tetramethyl-[1,3,2]dioxaborolane and 5-(4-bromo-3,5-dimethyl-phenyl)-2-methyl-2H-1,2,3,4-tetrazole following a procedure analogous to that described in Step 3 of Intermediate 2. Mass spectrum (ESI⁺): m/z=453 [M+H]⁺.

Step 2: (S)-4-[2,6-Dimethyl-4-(2-methyl-2H-tetrazol-5-yl)-phenyl]-7-fluoro-indan-1-ol The title compound is prepared from 5-{4-[(S)-1-(tert-Butyl-dimethyl-silanyloxy)-7-fluoro-indan-4-yl]-3,5-dimethyl-phenyl}-2-methyl-2H-tetrazole following a procedure analogous to that described in Step 4 of Intermediate 3. Mass spectrum (ESI⁺): m/z=339 [M+H]⁺.

Step 3: (R)-4-[2,6-Dimethyl-4-(2-methyl-2H-tetrazol-5-yl)-phenyl]-7-fluoro-indan-1-ylamine The title compound is prepared from (S)-4-[2,6-dimethyl-4-(2-methyl-2H-tetrazol-5-yl)-phenyl]-7-fluoro-indan-1-ol following a procedure analogous to that described in Step 5 of Intermediate 2. Mass spectrum (ESI⁺): m/z=364 [M+H]⁺.

Step 4: (R)-4-[2,6-Dimethyl-4-(2-methyl-2H-tetrazol-5-yl)-phenyl]-7-fluoro-indan-1-ylamine The title compound is prepared from (R)-4-[2,6-dimethyl-4-(2-methyl-2H-tetrazol-5-yl)-phenyl]-7-fluoro-indan-1-ylamine following a procedure analogous to that described in Step 6 of Intermediate 2. Mass spectrum (ESI⁺): m/z=338 [M+H]⁺.

Intermediate 5

(R)-4-[2,6-Dimethyl-4-(2-methyl-2H-tetrazol-5-yl)-phenyl]-indan-1-ylamine

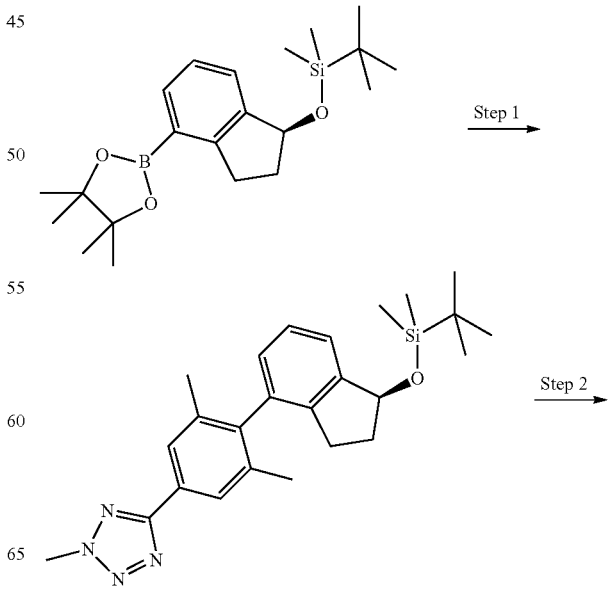

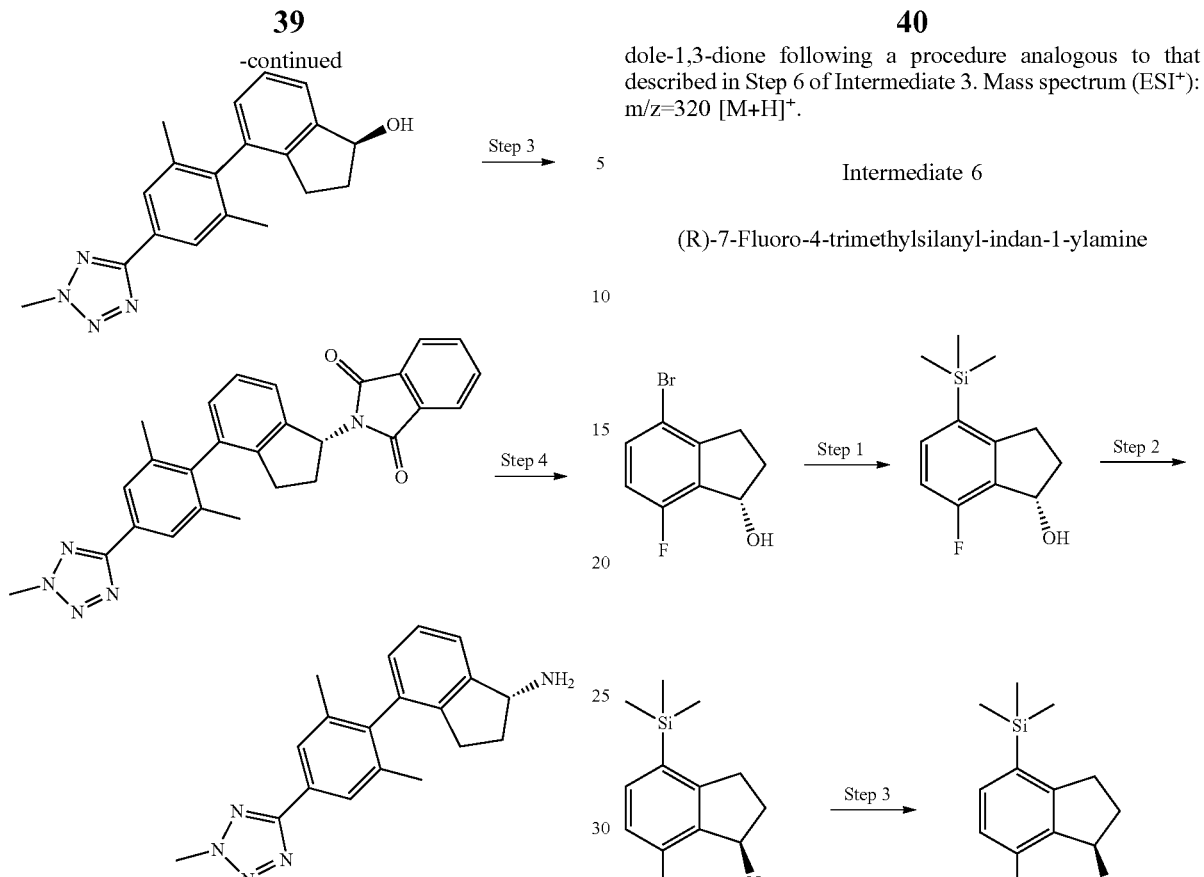

Step 1: 5-{4-[(S)-1-(tert-Butyl-dimethyl-silanyloxy)-indan-4-yl]-3,5-dimethyl-phenyl}-2-methyl-2H-tetrazole The title compound is prepared from 2-[(S)-1-(tert-butyl-dimethyl-silanyloxy)-indan-4-yl]-4,4,5,5-tetramethyl-[1,3,2]dioxaborolane and 5-(4-bromo-3,5-dimethylphenyl)-2-methyl-2H-1,2,3,4-tetrazole following a procedure analogous to that described in Step 3 of Intermediate 2. Mass spectrum (ESI$^+$): m/z=435 [M+H]$^+$.

Step 2: (S)-4-[2,6-Dimethyl-4-(2-methyl-2H-tetrazol-5-yl)-phenyl]-indan-1-ol

The title compound is prepared from 5-{4-[(S)-1-(tert-butyl-dimethyl-silanyloxy)-indan-4-yl]-3,5-dimethyl-phenyl}-2-methyl-2H-tetrazole following a procedure analogous to that described in Step 4 of Intermediate 3. Mass spectrum (ESI$^+$): m/z=321 [M+H]$^+$.

Step 3: 2-{(R)-4-[2,6-Dimethyl-4-(2-methyl-2H-tetrazol-5-yl)-phenyl]-indan-1-yl}-isoindole-1,3-dione The title compound is prepared from (S)-4-[2,6-dimethyl-4-(2-methyl-2H-tetrazol-5-yl)-phenyl]-indan-1-ol and phthalimide following a procedure analogous to that described in Step 5 of Intermediate 3. Mass spectrum (ESI$^+$): m/z=450 [M+H]$^+$.

Step 4: (R)-4-[2,6-Dimethyl-4-(2-methyl-2H-tetrazol-5-yl)-phenyl]-indan-1-ylamine The title compound is prepared 2-{(R)-4-[2,6-dimethyl-4-(2-methyl-2H-tetrazol-5-yl)-phenyl]-indan-1-yl}-isoindole-1,3-dione following a procedure analogous to that described in Step 6 of Intermediate 3. Mass spectrum (ESI$^+$): m/z=320 [M+H]$^+$.

Intermediate 6

(R)-7-Fluoro-4-trimethylsilanyl-indan-1-ylamine

Step 1: (S)-7-Fluoro-4-trimethylsilyl-indan-1-ol n-Butyl lithium (1.6 mol/L in hexanes; 60 mL) is added dropwise to a flask charged with a stir bar, (S)-4-bromo-7-fluoro-indan-1-ol (10.0 g), and tetrahydrofuran (80 mL) cooled to −75° C. The mixture is stirred below −70° C. for 45 min prior to the addition of chlorotrimethylsilane (12 mL). The mixture is warmed to room temperature overnight. The mixture is cooled to −50° C., treated with 4 M aqueous HCl solution (25 mL), and warmed to room temperature. The mixture is concentrated, and the residue is chromatographed on silica gel (cyclohexane/ethyl acetate 3:1→2:3) to give the title compound. Mass spectrum (ESI$^+$): m/z=207 [M-OH]$^+$.

Step 2: ((R)-1-Azido-7-fluoro-indan-4-yl)-trimethyl-silane

The title compound is prepared from (S)-7-fluoro-4-trimethylsilanyl-indan-1-ol following a procedure analogous to that described in Step 2 of Intermediate 8. Mass spectrum (ESI$^+$): m/z=207 [M−N$_3$]$^+$.

Step 3: (R)-7-Fluoro-4-trimethylsilyl-indan-1-ylamine

The title compound is prepared from ((R)-1-azido-7-fluoro-indan-4-yl)-trimethyl-silane following a procedure analogous to that described in Step 3 of Intermediate 8. Mass spectrum (ESI$^+$): m/z=224 [M+H]$^+$.

Intermediate 7

{(S)-3-[(R)-7-Fluoro-4-(4,4,5,5-tetramethyl-[1,3,2]dioxaborolan-2-yl)-indan-1-ylamino]-6,7-dihydro-5H-[2]pyrindin-7-yl}-acetic Acid Methyl Ester

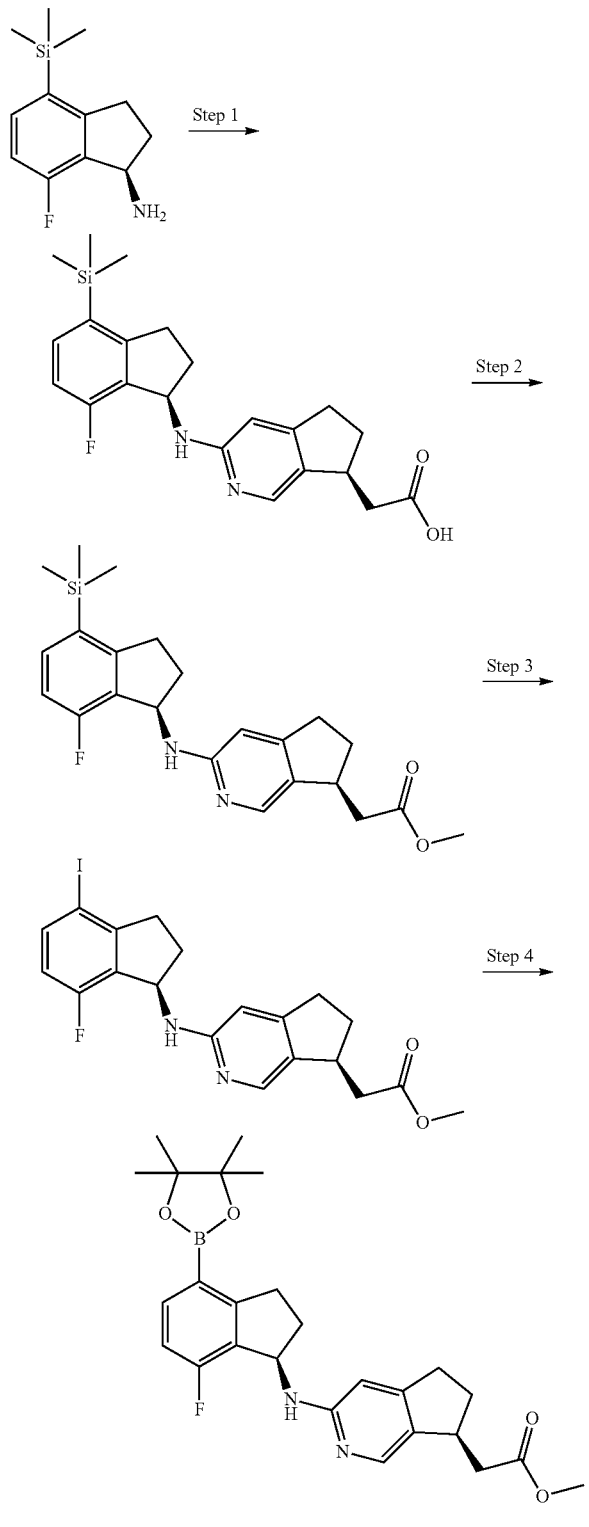

Step 1: [(S)-3-((R)-7-Fluoro-4-trimethylsilanyl-indan-1-ylamino)-6,7-dihydro-5H-[2]pyrindin-7-yl]-acetic Acid A vial charged with a stir bar, (R)-7-fluoro-4-trimethylsilyl-indan-1-ylamine (0.90 g), ((S)-3-chloro-6,7-dihydro-5H-[2]pyrindin-7-yl)-acetic acid ethyl ester (1.17 g), and 1,4-dioxane (15 mL) is purged with Ar for 10 min. Sodium tert-butoxide (0.97 g) and chloro[2-(dicyclohexylphosphino)-3,6-dimethoxy-2',4',6'-triisopropyl-1,1'-biphenyl][2-(2-aminoethyl)phenyl]palladium(II) (BRETTPHOS Pd G1 methyl-tert-butyl ether adduct; 64 mg) are added, and the mixture is stirred in a microwave oven at 100° C. for 40 min. After cooling to room temperature, methanol is added, and the resulting mixture is neutralized with HCl in 1,4-dioxane. Charcoal is added, and the mixture is filtered after stirring for 5 min. The filtrate is concentrated to give the crude title compound that is used as is in the next reaction step.

Step 2: [(S)-3-((R)-7-Fluoro-4-trimethylsilanyl-indan-1-ylamino)-6,7-dihydro-5H-[2]pyrindin-7-yl]-acetic Acid Methyl Ester HCl (4 mol/L in 1,4-dioxane; 1.5 mL) is added to a solution of [(S)-3-((R)-7-fluoro-4-trimethylsilanyl-indan-1-ylamino)-6,7-dihydro-5H-[2]pyrindin-7-yl]-acetic acid (1.42 g) in methanol (12 mL) at room temperature. The mixture is stirred at room temperature overnight. The mixture is concentrated, and the residue is chromatographed on silica gel (dichloromethane/methanol 97:3-3:1) to give the title compound. Mass spectrum (ESI$^+$): m/z=415 [M+H]$^+$.

Step 3: [(S)-3-((R)-7-Fluoro-4-iodo-indan-1-ylamino)-6,7-dihydro-5H-[2]pyrindin-7-yl]-acetic Acid Methyl Ester Iodine monochloride (1 mol/L in dichloromethane; 14 mL) is added to a solution of [(S)-3-((R)-7-fluoro-4-trimethylsilanyl-indan-1-ylamino)-6,7-dihydro-5H-[2]pyrindin-7-yl]-acetic acid methyl ester (2.90 g) in dichloromethane (5 mL) chilled in an ice bath. The solution is stirred in the cooling bath for 10 min. The mixture is diluted with aqueous Na$_2$S$_2$O$_3$ solution and aqueous NaHCO$_3$ solution, and the resulting mixture is extracted with dichloromethane. The combined extracts are washed with brine, dried (MgSO$_4$), and concentrated. The residue is chromatographed on silica gel (dichloromethane/methanol 98:2→3:1) to give the title compound. Mass spectrum (ESI$^+$): m/z=469 [M+H]$^+$.

Step 4: {(S)-3-[(R)-7-Fluoro-4-(4,4,5,5-tetramethyl-[1,3,2]dioxaborolan-2-yl)-indan-1-ylamino]-6,7-dihydro-5H-[2]pyrindin-7-yl}-acetic Acid Methyl Ester A flask charged with a stir bar, [(S)-3-((R)-7-fluoro-4-iodo-indan-1-ylamino)-6,7-dihydro-5H-[2]pyrindin-7-yl]-acetic acid methyl ester (2.64 g), bis-(pinacolato)-diboron (1.88 g), potassium acetate (1.38 g), and dimethylsulfoxide (20 mL) is purged with argon for 10 min. Pd(PPh$_3$)$_4$ (0.50 mg) is added, and the mixture is stirred at 110° C. for 2 h. After cooling to room temperature, aqueous NaHCO$_3$ solution is added, and the mixture is filtered over Celite. The filtrate is extracted with dichloromethane, and the combined extracts are washed with brine and concentrated. The residue is chromatographed on silica gel (dichloromethane/methanol 96:4) to give the title compound. Mass spectrum (ESI$^+$): m/z=469 [M+H]$^+$.

Example 1

((S)-6-{(R)-7-Fluoro-4-[4-(3-hydroxy-3-methyl-butoxy)-2,6-dimethyl-phenyl]-indan-1-ylamino}-2,3-dihydro-furo[3,2-c]pyridin-3-yl)-acetic Acid

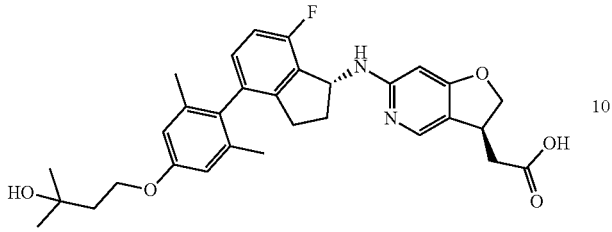

A vial charged with a stir bar, 4-[4-((R)-1-amino-7-fluoro-indan-4-yl)-3,5-dimethyl-phenoxy]-2-methyl-butan-2-ol (40 mg), (S)-6-chloro-2,3-dihydro-furo[3,2-c]pyridin-3-yl)-acetic acid ethyl ester (32 mg), sodium tert-butoxide (27 mg), and 1,4-dioxane (3 mL) is purged with argon for 10 min. BrettPhos Pd G1 methyl-tert-butyl ether adduct (4.5 mg) is added, the vial is sealed, and the mixture is stirred at 100° C. for 40 min. After cooling to room temperature, aqueous 10 N KOH solution (0.5 mL) is added, and the mixture is stirred at 45° C. for 30 min. The mixture is chromatographed (HPLC) to give the title compound. LC (method 1): $t_R$=0.97 min; Mass spectrum (ESI$^+$): m/z=535 [M+H]$^+$.

Example 2

((R)-6-{(R)-7-Fluoro-4-[4-(3-hydroxy-3-methyl-butoxy)-2,6-dimethyl-phenyl]-indan-1-ylamino}-2,3-dihydro-furo[3,2-c]pyridin-3-yl)-acetic Acid

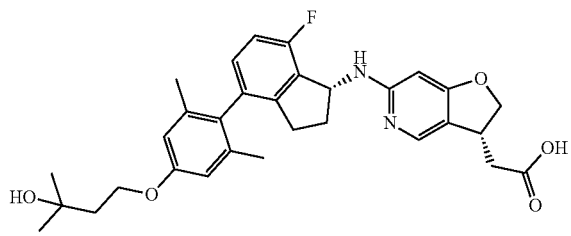 [SMILES: Cc1cc(OCCC(C)(C)O)cc(C)c1-c1ccc(F)c2c1CC[C@H]2Nc1cc2c(cn1)[C@@H](CC(=O)O)CO2]

The title compound is prepared from 4-[4-((R)-1-amino-7-fluoro-indan-4-yl)-3,5-dimethyl-phenoxy]-2-methyl-butan-2-ol and (R)-6-chloro-2,3-dihydro-furo[3,2-c]pyridin-3-yl)-acetic acid ethyl ester following a procedure analogous to that described for Example 1. LC (method 1): $t_R$=0.96 min; Mass spectrum (ESI$^+$): m/z=535 [M+H]$^+$.

Example 3

((S)-6-{(R)-4-[4-(3-Hydroxy-3-methyl-butoxy)-2,6-dimethyl-phenyl]-indan-1-ylamino}-2,3-dihydro-furo[3,2-c]pyridin-3-yl)-acetic Acid

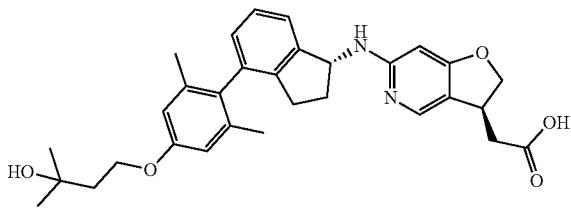 [SMILES: Cc1cc(OCCC(C)(C)O)cc(C)c1-c1cccc2c1CC[C@H]2Nc1cc2c(cn1)[C@H](CC(=O)O)CO2]

The title compound is prepared from 4-[4-((R)-1-amino-indan-4-yl)-3,5-dimethyl-phenoxy]-2-methyl-butan-2-ol and (S)-6-chloro-2,3-dihydro-furo[3,2-c]pyridin-3-yl)-acetic acid ethyl ester following a procedure analogous to that described for Example 1. LC (method 1): $t_R$=0.96 min; Mass spectrum (ESI$^+$): m/z=517 [M+H]$^+$.

Example 4

((R)-6-{(R)-4-[4-(3-Hydroxy-3-methyl-butoxy)-2,6-dimethyl-phenyl]-indan-1-ylamino}-2,3-dihydro-furo[3,2-c]pyridin-3-yl)-acetic acid

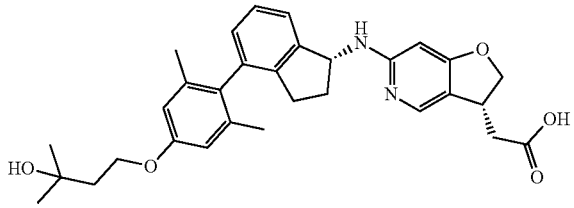 [SMILES: Cc1cc(OCCC(C)(C)O)cc(C)c1-c1cccc2c1CC[C@H]2Nc1cc2c(cn1)[C@@H](CC(=O)O)CO2]

The title compound is prepared from 4-[4-((R)-1-amino-indan-4-yl)-3,5-dimethyl-phenoxy]-2-methyl-butan-2-ol and (R)-6-chloro-2,3-dihydro-furo[3,2-c]pyridin-3-yl)-acetic acid ethyl ester following a procedure analogous to that described for Example 1. LC (method 1): $t_R$=0.96 min; Mass spectrum (ESI$^+$): m/z=517 [M+H]$^+$.

Example 5

((S)-6-{(R)-4-[2,6-Dimethyl-4-(2-methyl-2H-tetrazol-5-yl)-phenyl]-7-fluoro-indan-1-ylamino}-2,3-dihydro-furo[3,2-c]pyridin-3-yl)-acetic Acid

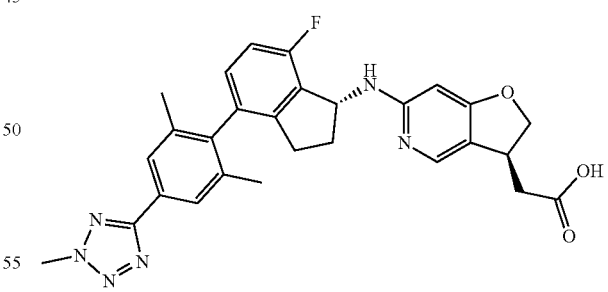

The title compound is prepared from (R)-4-[2,6-dimethyl-4-(2-methyl-2H-tetrazol-5-yl)-phenyl]-7-fluoro-indan-1-ylamine and (S)-6-chloro-2,3-dihydro-furo[3,2-c]pyridin-3-yl)-acetic acid ethyl ester following a procedure analogous to that described for Example 1. LC (method 1): $t_R$=0.95 min; Mass spectrum (ESI$^+$): m/z=515 [M+H]$^+$.

Example 6

((R)-6-{(R)-4-[2,6-Dimethyl-4-(2-methyl-2H-tetrazol-5-yl)-phenyl]-7-fluoro-indan-1-ylamino}-2,3-dihydro-furo[3,2-c]pyridin-3-yl)-acetic Acid

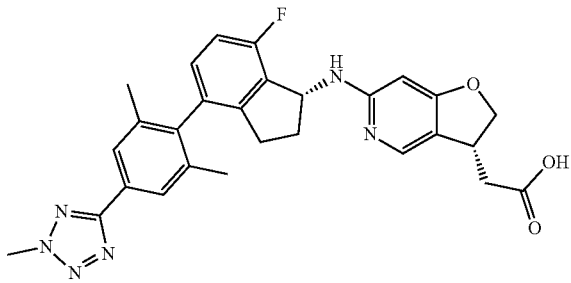 [SMILES: Cc1cc(-c2nnn(C)n2)cc(C)c1-c1ccc(F)c2c1CC[C@H]2Nc1cc2c(cn1)[C@@H](CC(=O)O)CO2]

The title compound is prepared from (R)-4-[2,6-dimethyl-4-(2-methyl-2H-tetrazol-5-yl)-phenyl]-7-fluoro-indan-1-ylamine and (R)-6-chloro-2,3-dihydro-furo[3,2-c]pyridin-3-yl)-acetic acid ethyl ester following a procedure analogous to that described for Example 1. LC (method 1): $t_R$=0.94 min; Mass spectrum (ESI$^+$): m/z=515 [M+H]$^+$.

Example 7

((S)-6-{(R)-4-[2,6-Dimethyl-4-(2-methyl-2H-tetrazol-5-yl)-phenyl]-indan-1-ylamino}-2,3-dihydro-furo[3,2-c]pyridin-3-yl)-acetic Acid

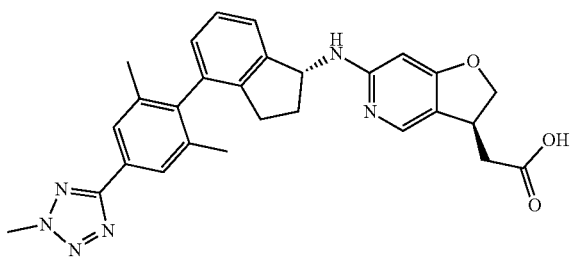 [SMILES: Cc1cc(-c2nnn(C)n2)cc(C)c1-c1cccc2c1CC[C@H]2Nc1cc2c(cn1)[C@H](CC(=O)O)CO2]

The title compound is prepared from (R)-4-[2,6-dimethyl-4-(2-methyl-2H-tetrazol-5-yl)-phenyl]-indan-1-ylamine and ethyl (S)-6-chloro-2,3-dihydro-furo[3,2-c]pyridin-3-yl)-acetic acid ethyl ester following a procedure analogous to that described for Example 1. LC (method 1): $t_R$=0.94 min; Mass spectrum (ESI$^+$): m/z=497 [M+H]$^+$.

Example 8

((R)-6-{(R)-4-[2,6-Dimethyl-4-(2-methyl-2H-tetrazol-5-yl)-phenyl]-indan-1-ylamino}-2,3-dihydro-furo[3,2-c]pyridin-3-yl)-acetic acid

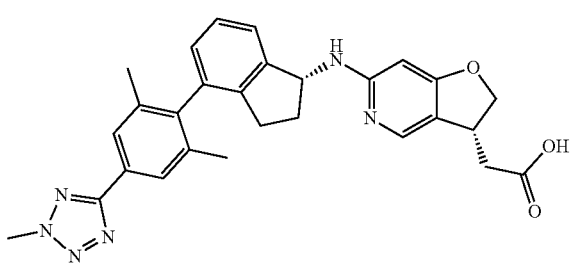 [SMILES: Cc1cc(-c2nnn(C)n2)cc(C)c1-c1cccc2c1CC[C@H]2Nc1cc2c(cn1)[C@@H](CC(=O)O)CO2]

The title compound is prepared from (R)-4-[2,6-dimethyl-4-(2-methyl-2H-tetrazol-5-yl)-phenyl]-indan-1-ylamine and ethyl (R)-6-chloro-2,3-dihydro-furo[3,2-c]pyridin-3-yl)-acetic acid ethyl ester following a procedure analogous to that described for Example 1. LC (method 2): $t_R$=0.87 min; Mass spectrum (ESI$^+$): m/z=497 [M+H]$^+$.

Example 9

[(S)-6-((R)-4-{2,6-Dimethyl-4-[(R)-(tetrahydro-furan-3-yl)oxy]-phenyl}-7-fluoro-indan-1-ylamino)-2,3-dihydro-furo[3,2-c]pyridin-3-yl]-acetic Acid

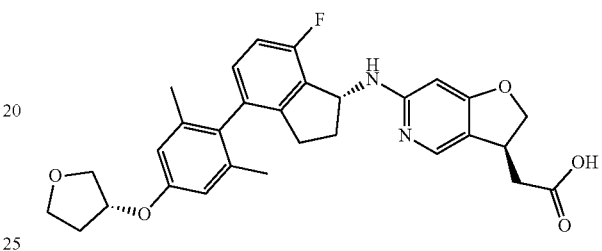

A vial charged with a stir bar, {(S)-3-[(R)-7-fluoro-4-(4,4,5,5-tetramethyl-[1,3,2]dioxaborolan-2-yl)-indan-1-ylamino]-6,7-dihydro-5H-[2]pyrindin-7-yl}-acetic acid methyl ester (50 mg), (R)-3-(4-bromo-3,5-dimethyl-phenoxy)-tetrahydrofuran (43 mg), and N,N-dimethylformamide (1 mL) is purged with argon for 10 min. Cs$_2$CO$_3$ (2 mol/L in water; 0.16 mL) and 1,1'-bis(di-tert-butylphosphino)-ferrocene-palladium dichloride (7 mg) is added, and the mixture is stirred at 110° C. for 1 h. After cooling to room temperature, aqueous 4 N KOH solution (0.2 mL) is added, and the mixture is stirred at 50° C. for 3 h. The mixture is chromatographed (HPLC; acetonitrile/water/ammonium hydroxide) to give the title compound. LC (method 3): $t_R$=0.59 min; Mass spectrum (ESI$^+$): m/z=519 [M+H]$^+$.

Example 10

((S)-6-{(R)-4-[2,6-Dimethyl-4-(tetrahydro-pyran-4-yloxy)-phenyl]-7-fluoro-indan-1-ylamino}-2,3-dihydro-furo[3,2-c]pyridin-3-yl)-acetic Acid

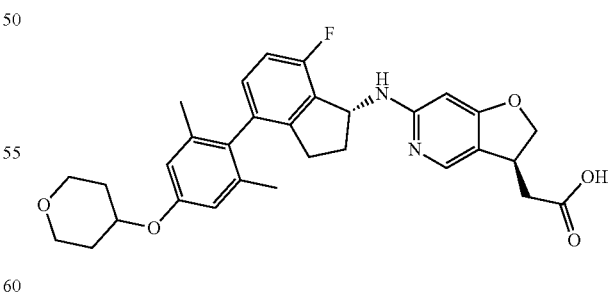

The title compound is prepared from {(S)-3-[(R)-7-fluoro-4-(4,4,5,5-tetramethyl-[1,3,2]dioxaborolan-2-yl)-indan-1-ylamino]-6,7-dihydro-5H-[2]pyrindin-7-yl}-acetic acid methyl ester and 4-(4-bromo-3,5-dimethyl-phenoxy)-tetrahydropyran following a procedure analogous to that described for Example 9. LC (method 3): $t_R$=0.62 min; Mass spectrum (ESI$^+$): m/z=533 [M+H]$^+$.

Example 11

((S)-6-{(R)-4-[2,6-Dimethyl-4-(3-methyl-oxetan-3-ylmethoxy)-phenyl]-7-fluoro-indan-1-ylamino}-2,3-dihydro-furo[3,2-c]pyridin-3-yl)-acetic Acid

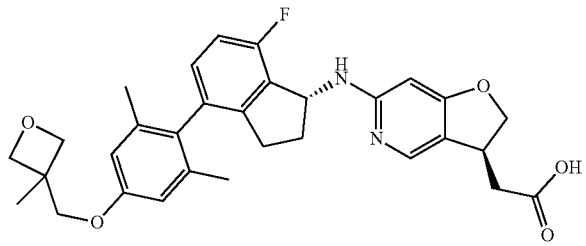 [SMILES: Cc1cc(OCC2(C)COC2)cc(C)c1-c1ccc(F)c2c1CC[C@H]2Nc1cc2c(cn1)[C@H](CC(=O)O)CO2]

The title compound is prepared from {(S)-3-[(R)-7-fluoro-4-(4,4,5,5-tetramethyl-[1,3,2]dioxaborolan-2-yl)-indan-1-ylamino]-6,7-dihydro-5H-[2]pyrindin-7-yl}-acetic acid methyl ester and 3-(4-bromo-3,5-dimethyl-phenoxymethyl)-3-methyl-oxetane following a procedure analogous to that described for Example 9. LC (method 3): $t_R$=0.63 min; Mass spectrum (ESI$^+$): m/z=533 [M+H]$^+$.

Example 12

[(S)-6-((R)-4-{2,6-Dimethyl-4-[(S)-(tetrahydro-furan-3-yl)oxy]-phenyl}-7-fluoro-indan-1-ylamino)-2,3-dihydro-furo[3,2-c]pyridin-3-yl]-acetic Acid

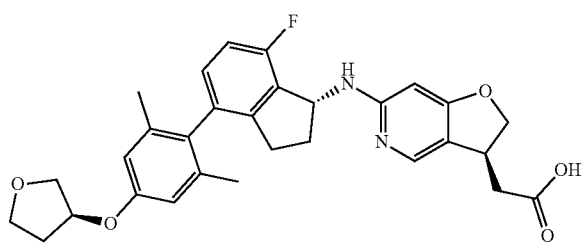 [SMILES: Cc1cc(O[C@H]2CCOC2)cc(C)c1-c1ccc(F)c2c1CC[C@H]2Nc1cc2c(cn1)[C@H](CC(=O)O)CO2]

The title compound is prepared from {(S)-3-[(R)-7-fluoro-4-(4,4,5,5-tetramethyl-[1,3,2]dioxaborolan-2-yl)-indan-1-ylamino]-6,7-dihydro-5H-[2]pyrindin-7-yl}-acetic acid methyl ester and (S)-3-(4-bromo-3,5-dimethyl-phenoxy)-tetrahydrofuran following a procedure analogous to that described for Example 9. LC (method 3): $t_R$=0.59 min; Mass spectrum (ESI$^+$): m/z=519 [M+H]$^+$.

Example 13

((S)-6-{(R)-7-Fluoro-4-[4-(2-hydroxo-2-methyl-propoxy)-2,6-dimethyl-phenyl]-indan-1-ylamino}-2,3-dihydro-furo[3,2-c]pyridin-3-yl)-acetic Acid

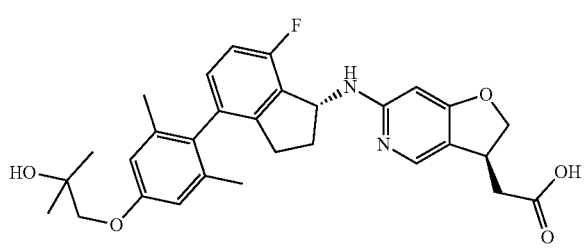 [SMILES: Cc1cc(OCC(C)(C)O)cc(C)c1-c1ccc(F)c2c1CC[C@H]2Nc1cc2c(cn1)[C@H](CC(=O)O)CO2]

The title compound is prepared from {(S)-3-[(R)-7-fluoro-4-(4,4,5,5-tetramethyl-[1,3,2]dioxaborolan-2-yl)-indan-1-ylamino]-6,7-dihydro-5H-[2]pyrindin-7-yl}-acetic acid methyl ester and 1-(4-bromo-3,5-dimethyl-phenoxy)-2-methyl-propan-2-ol following a procedure analogous to that described for Example 9. LC (method 4): $t_R$=0.82 min; Mass spectrum (ESI$^+$): m/z=521 [M+H]$^+$.

Example 14

((S)-6-{(R)-4-[2,6-Dimethyl-4-(tetrahydro-furan-3-ylmethoxy)-phenyl]-7-fluoro-indan-1-ylamino}-2,3-dihydro-furo[3,2-c]pyridin-3-yl)-acetic Acid

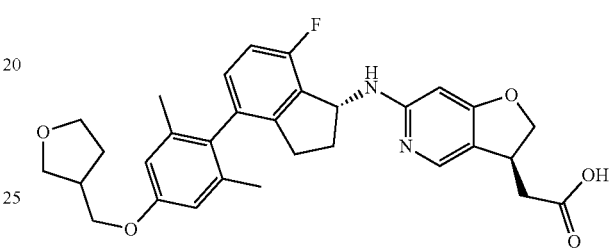

The title compound is prepared from (R)-7-fluoro-1-((S)-7-methoxycarbonylmethyl-6,7-dihydro-5H-[2]pyrindin-3-ylamino)-indan-4-boronic acid and 3-(4-bromo-3,5-dimethyl-phenoxymethyl)-tetrahydrofuran following a procedure analogous to that described for Example 9. LC (method 3): $t_R$=0.73 min; Mass spectrum (ESI$^+$): m/z=533 [M+H]$^+$.

Example 15

[(S)-6-((R)-7-Fluoro-4-{4-[2-(2-hydroxo-2-methyl-propyl)-2H-tetrazol-5-yl]-2,6-dimethyl-phenyl}-indan-1-ylamino)-2,3-dihydro-furo[3,2-c]pyridin-3-yl]-acetic acid

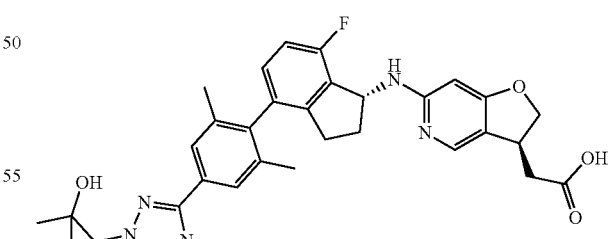

The title compound is prepared from (R)-7-fluoro-1-((S)-7-methoxycarbonylmethyl-6,7-dihydro-5H-[2]pyrindin-3-ylamino)-indan-4-boronic acid and 1-[5-(4-bromo-3,5-dimethyl-phenyl)-tetrazol-2-yl]-2-methyl-propan-2-ol following a procedure analogous to that described for Example 9. LC (method 3): $t_R$=0.56 min; Mass spectrum (ESI$^+$): m/z=573 [M+H]$^+$.

Example 16

((S)-6-{(R)-4-[2,6-Dimethyl-4-(1-methyl-2-oxo-1,2-dihydro-pyrimidin-4-yl)-phenyl]-7-fluoro-indan-1-ylamino}-2,3-dihydro-furo[3,2-c]pyridin-3-yl)-acetic acid

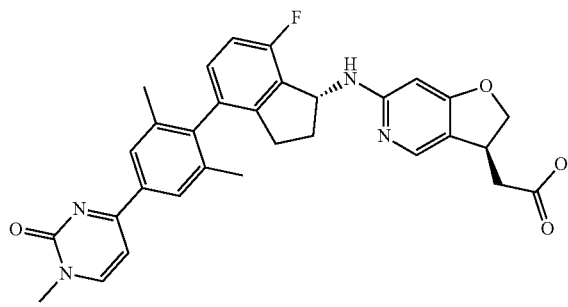

The title compound is prepared from (R)-7-fluoro-1-((S)-7-methoxycarbonylmethyl-6,7-dihydro-5H-[2]pyrindin-3-ylamino)-indan-4-boronic acid and 4-(4-iodo-3,5-dimethyl-phenyl)-1-methyl-1H-pyrimidin-2-one following a procedure analogous to that described for Example 9. LC (method 3): $t_R$=0.48 min; Mass spectrum (ESI$^+$): m/z=541 [M+H]$^+$.

Example 17

((S)-6-{(R)-4-[2,6-Dimethyl-4-(1-methyl-2-oxo-1,2-dihydro-pyridin-4-yl)-phenyl]-7-fluoro-indan-1-ylamino}-2,3-dihydro-furo[3,2-c]pyridin-3-yl)-acetic Acid

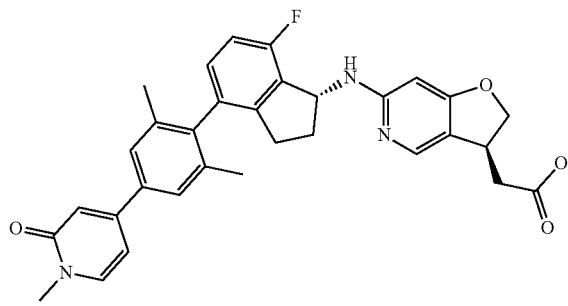

The title compound is prepared from (R)-7-fluoro-1-((S)-7-methoxycarbonylmethyl-6,7-dihydro-5H-[2]pyrindin-3-ylamino)-indan-4-boronic acid and 4-(4-bromo-3,5-dimethyl-phenyl)-1-methyl-1H-pyridin-2-one following a procedure analogous to that described for Example 9. LC (method 3): $t_R$=0.52 min; Mass spectrum (ESI$^+$): m/z=540 [M+H]$^+$.

Example 18

((S)-6-{(R)-4-[2,6-Dimethyl-4-(1-methyl-6-oxo-1,6-dihydro-pyrimidin-4-yl)-phenyl]-7-fluoro-indan-1-ylamino}-2,3-dihydro-furo[3,2-c]pyridin-3-yl)-acetic Acid

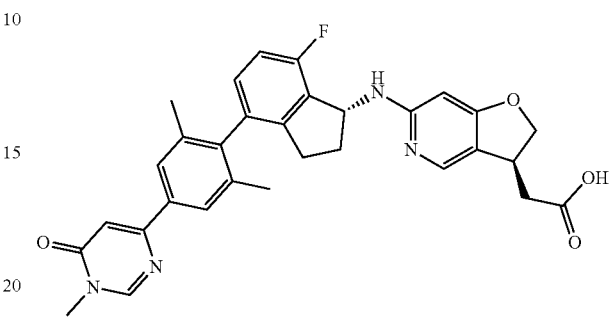

The title compound is prepared from (R)-7-fluoro-1-((S)-7-methoxycarbonylmethyl-6,7-dihydro-5H-[2]pyrindin-3-ylamino)-indan-4-boronic acid and 6-(4-iodo-3,5-dimethyl-phenyl)-3-methyl-3H-pyrimidin-4-one following a procedure analogous to that described for Example 9. LC (method 4): $t_R$=0.76 min; Mass spectrum (ESI$^+$): m/z=541 [M+H]$^+$.

Example 19

((S)-6-{(R)-4-[2,6-Dimethyl-4-(1-methyl-6-oxo-1,6-dihydro-pyridin-3-yl)-phenyl]-7-fluoro-indan-1-ylamino}-2,3-dihydro-furo[3,2-c]pyridin-3-yl)-acetic Acid

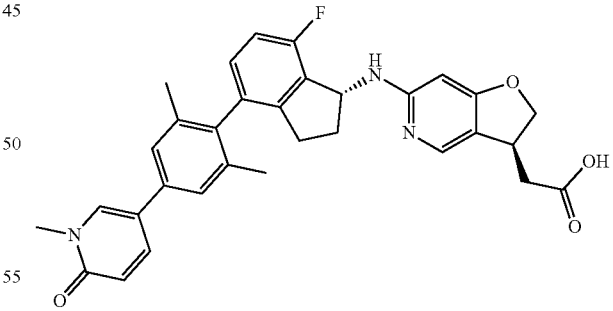

The title compound is prepared from (R)-7-fluoro-1-((S)-7-methoxycarbonylmethyl-6,7-dihydro-5H-[2]pyrindin-3-ylamino)-indan-4-boronic acid and 5-(4-bromo-3,5-dimethyl-phenyl)-1-methyl-1H-pyridin-2-one following a procedure analogous to that described for Example 9. LC (method 4): $t_R$=0.78 min; Mass spectrum (ESI$^+$): m/z=540 [M+H]$^+$.

Example 20

{(S)-6-[(R)-4-(2,6-Dimethyl-4-pyrazin-2-yl-phenyl)-7-fluoro-indan-1-ylamino]-2,3-dihydro-furo[3,2-c]pyridin-3-yl}-acetic acid

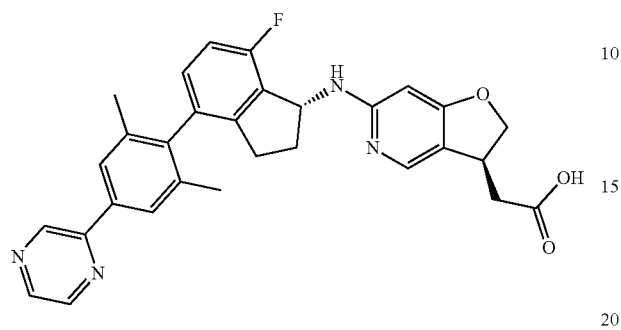

The title compound is prepared from (R)-7-fluoro-1-((S)-7-methoxycarbonylmethyl-6,7-dihydro-5H-[2]pyrindin-3-ylamino)-indan-4-boronic acid and 2-(4-chloro-3,5-dimethyl-phenyl)-pyrazine following a procedure analogous to that described for Example 9. LC (method 4): $t_R$=0.81 min; Mass spectrum (ESI$^+$): m/z=511 [M+H]$^+$.

The invention claimed is:

1. A compound of formula (I)

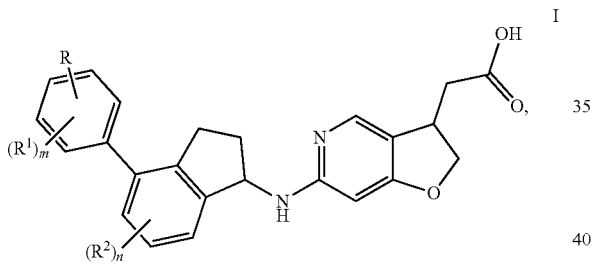

wherein

R is selected from the group consisting of
H, F, Cl, Br, I, $C_{1-6}$-alkyl, $C_{2-6}$-alkenyl, $C_{2-6}$-alkynyl, $C_{3-6}$-cycloalkyl, NC—, HNR$^N$—C(=O)—, $C_{1-4}$-alkyl-NR$^N$—C(=O)—, $C_{3-6}$-cycloalkyl-NR$^N$—C(=O)—, heterocyclyl-NR$^N$—C(=O)—, heteroaryl-NR$^N$—C(=O)—, HOOC—, $C_{1-4}$-alkyl-O—C(=O)—, O$_2$N—, HR$^N$N—, $C_{1-4}$-alkyl-R$^N$N—, $C_{1-4}$-alkyl-C(=O)NR$^N$—, $C_{3-6}$-cycloalkyl-C(=O)NR$^N$—, heterocyclyl-C(=O)—NR$^N$—, heteroaryl-C(=O)NR$^N$—, $C_{1-4}$-alkyl-S(=O)$_2$NR$^N$—, $C_{3-6}$-cycloalkyl-S(=O)$_2$NR$^N$—, heterocyclyl-S(=O)$_2$NR$^N$—, heteroaryl-S(=O)$_2$NR$^N$—, HO—, $C_{1-6}$-alkyl-O—, HOOC—$C_{1-3}$-alkyl-O—, heterocyclyl-$C_{1-3}$-alkyl-O—, phenyl-$C_{1-3}$-alkyl-O—, $C_{3-6}$-cycloalkyl-O—, heterocyclyl-O—, heteroaryl-O—, $C_{1-4}$-alkyl-S—, $C_{3-6}$-cycloalkyl-S—, heterocyclyl-S—, $C_{1-4}$-alkyl-S(=O)—, $C_{3-6}$-cycloalkyl-S(=O)—, heterocyclyl-S(=O)—, $C_{1-4}$-alkyl-S(=O)$_2$—, $C_{3-6}$-cycloalkyl-S(=O)$_2$—, heterocyclyl-S(=O)$_2$—, phenyl-S(=O)$_2$—, heteroaryl-S(=O)$_2$—, HNR$^N$—S(=O)$_2$—, $C_{1-4}$-alkyl-NR$^N$—S(=O)$_2$—, heterocyclyl, phenyl, and heteroaryl,
wherein each alkyl, cycloalkyl, and heterocyclyl group or sub-group within the group of residues mentioned for R is optionally substituted with 1 or more F atoms and optionally substituted with 1 to 3 groups independently selected from Cl, $C_{1-3}$-alkyl, NC—, (R$^N$)$_2$N—, HO—, $C_{1-3}$-alkyl-O—, and $C_{1-3}$-alkyl-S(=O)$_2$—; and
wherein each phenyl and heteroaryl group or sub-group within the group of residues mentioned for R is optionally substituted with 1 to 5 substituents independently selected from F, Cl, $C_{1-3}$-alkyl, HF$_2$C—, F$_3$C—, NC—, (R$^N$)$_2$N—, HO—, $C_{1-3}$-alkyl-O—, F$_3$C—O—, and $C_{1-3}$-alkyl-S(=O)$_2$—;
wherein each heterocyclyl group or sub-group within the group of residues mentioned for R is selected from
a cyclobutyl group wherein 1 CH$_2$ group is replaced by —NR$^N$— or —O—;
a $C_{5-6}$-cycloalkyl group wherein 1 CH$_2$ group is replaced by —C(=O)—, —NR$^N$—, —O—, —S—, or —S(=O)$_2$— and/or 1 CH group is replaced by N;
a $C_{5-6}$-cycloalkyl group wherein 1 CH$_2$ group is replaced by —NR$^N$— or —O—, a second CH$_2$ group is replaced by —NR$^N$—, —C(=O)— or —S(=O)$_2$— and/or 1 CH group is replaced by N; and
a $C_{5-6}$-cycloalkyl group wherein 2 CH$_2$ groups are replaced by —NR$^N$— or 1 CH$_2$ group by —NR$^N$— and the other by —O— and a third CH$_2$ group is replaced by —C(=O)— or —S(=O)$_2$— and/or 1 CH group is replaced by N;
wherein each heteroaryl group or sub-group within the group of residues mentioned for R is selected from tetrazolyl and a 5- or 6-membered heteroaromatic ring which contains 1, 2, or 3 heteroatoms independently of each other selected from =N—, —NR$^N$—, —O—, and —S—, wherein in heteroaromatic groups containing a —HC=N— unit this group is optionally replaced by —NR$^N$—C(=O)—;
wherein in heteroaryl and heterocyclyl rings with one or more NH groups, each of said NH groups is replaced by NR$^N$;
R$^1$ is selected from the group consisting of H, F, Cl, $C_{1-4}$-alkyl, $C_{3-6}$-cycloalkyl-, HO—$C_{1-4}$-alkyl, $C_{1-4}$-alkyl-O—$C_{1-4}$-alkyl, NC—, HO—, $C_{1-4}$-alkyl-O—, $C_{3-6}$-cycloalkyl-O—, $C_{1-4}$-alkyl-S—, $C_{1-4}$-alkyl-S(O)—, and $C_{1-4}$-alkyl-S(O)$_2$—,
wherein any alkyl and cycloalkyl group or sub-group within the group of residues mentioned for R$^1$ is optionally substituted with 1 or more F atoms, and wherein multiple R$^1$ may be identical or different if m is 2, 3 or 4;
m is an integer selected from 1, 2, 3, and 4;
R$^2$ is selected from the group consisting of H, F, Cl, $C_{1-4}$-alkyl, NC—, and $C_{1-4}$-alkyloxy,
wherein any alkyl group or sub-group within the group of residues mentioned for R$^2$ is optionally substituted with 1 or more F atoms, and wherein multiple R$^2$ may be identical or different if n is 2 or 3;
n is an integer selected from 1, 2, and 3;
R$^N$ is independently of each other selected from the group consisting of H, $C_{1-4}$-alkyl, HO—$C_{1-4}$-alkyl-(H$_2$C)—, $C_{1-3}$-alkyl-O—$C_{1-4}$-alkyl-, $C_{1-4}$-alkyl-C(=O)—, $C_{1-4}$-alkyl-NH—C(=O)—, $C_{1-4}$-alkyl-N($C_{1-4}$-alkyl)-C(=O)—, $C_{1-4}$-alkyl-O—C(=O)—, and $C_{1-4}$-alkyl-S(=O)$_2$—, wherein each alkyl group or sub-group within the group of residues mentioned for $R^N$ is optionally substituted with 1 or more F atoms;
wherein in any definition mentioned hereinbefore, if not specified otherwise, any alkyl group or sub-group may be straight-chained or branched,
or a salt thereof.

2. The compound according to claim 1, wherein
R is selected from the group consisting of H, F, Cl, $C_{1-4}$-alkyl, $C_3$-cycloalkyl, NC—, $H_2N$—C(=O)—, $C_{1-3}$-alkyl-$NR^N$—C(=O)—, HOOC—, $H_2N$—, $C_{1-3}$-alkyl-C(=O)$NR^N$—, $C_{1-4}$-alkyl-S(=O)$_2NR^N$—, HO—, $C_{1-5}$-alkyl-O—, HOOC—$CH_2$—O—, heterocyclyl-$CH_2$—O—, phenyl-$CH_2$—O—, $C_{3-6}$-cycloalkyl-O—, heterocyclyl-O—, heteroaryl-O—, heterocyclyl-S(=O)$_2$—, heterocyclyl, and heteroaryl,
wherein each alkyl, cycloalkyl, and heterocyclyl group or sub-group within the group of residues mentioned for R is optionally substituted with 1 or more F atoms and optionally substituted with 1 group selected from Cl, $H_3C$—, NC—, $R^N$HN—, HO—, $H_3C$—O—, and $H_3C$—S(=O)$_2$—;
wherein each heteroaryl group or sub-group within the group of residues mentioned for R is optionally substituted with 1 to 2 substituents independently selected from F, Cl, $H_3C$—, $F_3C$—, NC—, $(R^N)_2N$—, HO—, $H_3C$—O—, $F_3C$—O—, and $H_3C$—S(=O)$_2$—;
wherein each heterocyclyl or sub-group within the group of residues mentioned for R is selected from
a cyclobutyl group wherein 1 $CH_2$ group is replaced by —$NR^N$— or —O—;
a $C_{5-6}$-cycloalkyl group wherein 1 $CH_2$ group is replaced by —C(=O)—, —$NR^N$—, —O—, —S— or —S(=O)$_2$— and/or 1 CH group is replaced by N;
wherein each heteroaryl group or sub-group within the group of residues mentioned for R is selected from tetrazolyl, a 5-membered heteroaromatic ring which contains 1, 2 or 3 heteroatoms independently of each other selected from =N—, —NH—, O and S, and a 6-membered heteroaromatic ring which contains 1 or 2 =N— atoms, wherein a —HC=N— unit is optionally replaced by —NH—C(=O)—;
and wherein in each heteroaryl and heterocyclyl group or sub-group mentioned for R containing one or more NH, said NH group(s) is/are replaced by $NR^N$;
or a salt thereof.

3. The compound according to claim 1, wherein
R is selected from the group consisting of $H_3C$—O— monosubstituted with $C_{1-4}$-alkyl, oxetanyl, or tetrahydrofuranyl,
wherein the $C_{1-4}$-alkyl group attached to $H_3C$—O— is optionally monosubstituted with HO—, and
wherein said oxetanyl and tetrahydrofuranyl are optionally monosubstituted with $H_3C$—;
tetrahydrofuranyl-O— and tetrahydropyranyl-O—; and
a heteroaryl group selected from tetrazolyl, pyridin-2-onyl, pyrazinyl, pyrimidin-2-onyl, and pyrimidin-4-onyl,
wherein each of said heteroaryl groups is optionally monosubstituted with $H_3C$—, and
wherein each H—N group in said heteroaryl groups is optionally replaced with $H_3C$—N or $(H_3C)_2C(OH)$—$H_2C$—N;
or a salt thereof.

4. The compound according to claim 1, wherein
$R^1$ is H, F, Cl, $H_3C$—, $H_3C$—$H_2C$—, $(H_3C)_2CH$—, $F_3C$—, or $H_3C$—O—;
$R^2$ is H or F;
m is 2 and
n is 1;
or a salt thereof.

5. The compound according to claim 1, wherein $R^1$ is $H_3C$—; or a salt thereof.

6. The compound according to claim 1, wherein R is selected from the group consisting of

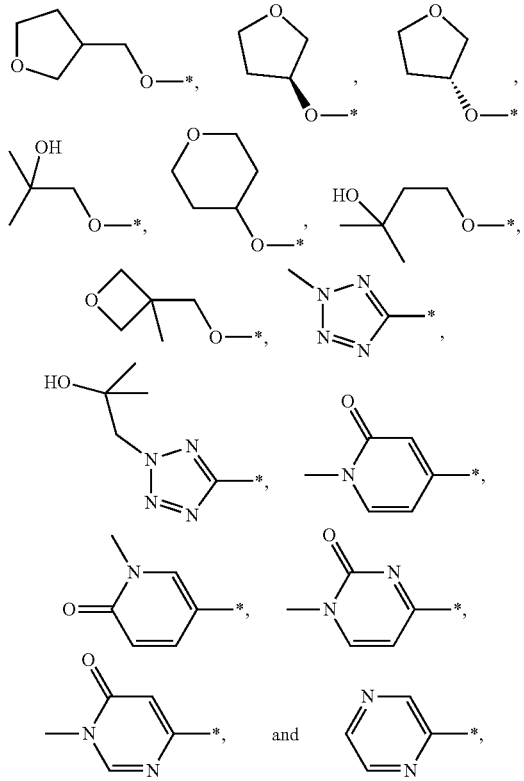

wherein the asterisk (-*) indicates the site/point of attachment;
$R^1$ is $H_3C$—;
m is 2;
$R^2$ is H or F;
n is 1; and
or a salt thereof.

7. The compound according to claim 1, with the structure and stereochemistry shown in formulae I.1, I.2, I.3, or I.4

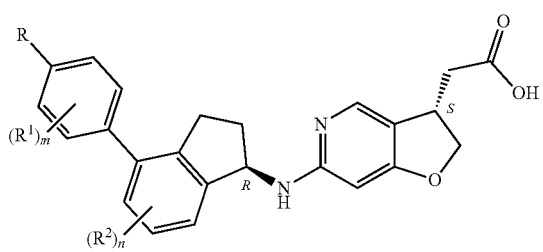

-continued

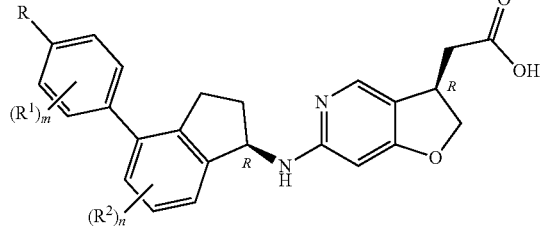
I.2

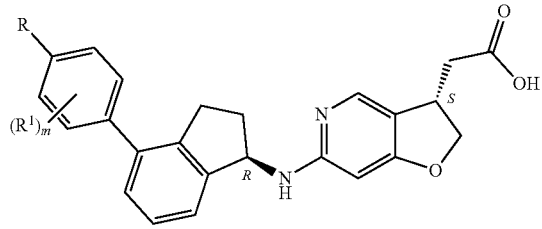
I.3

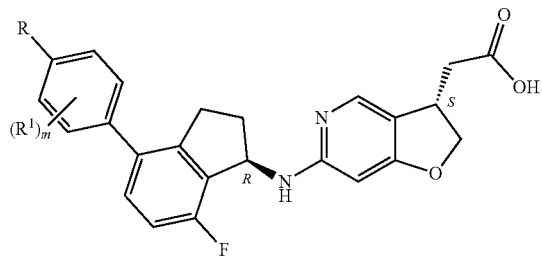
I.4 or a salt thereof.

8. A compound having one of the following structures:

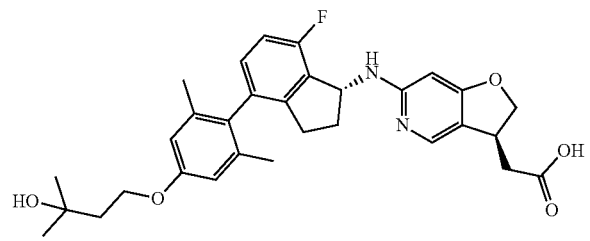

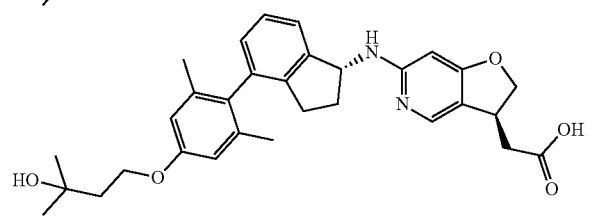

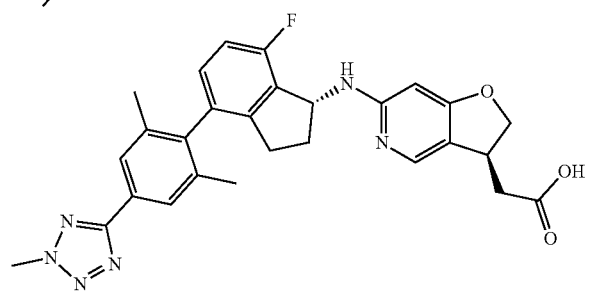

-continued

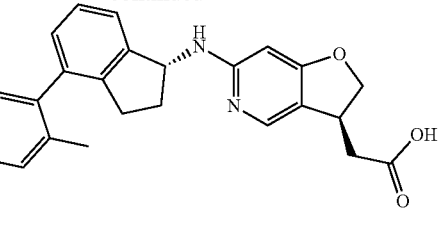

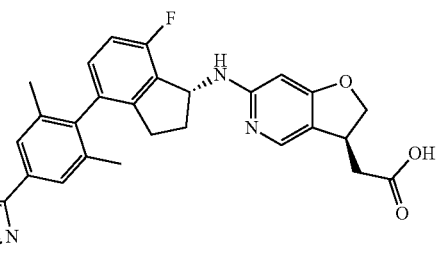

or a salt thereof.

9. A pharmaceutically acceptable salt of a compound according to claim 1.

10. A pharmaceutical composition comprising one or more compounds according to claim 1 or one or more pharmaceutically acceptable salts thereof, optionally together with one or more inert carriers and/or diluents.

11. A method for treating a disease or condition which can be influenced by the modulation of the function of GPR40, the method comprising administering to a patient in need thereof a compound according to claim 1, or a pharmaceutically acceptable salt thereof, wherein the disease or condition is a metabolic disease selected from the group consisting of type 2 diabetes mellitus, insulin resistance, obesity, cardiovascular disease and dyslipidemia.

12. A pharmaceutical composition comprising one or more compounds according to claim 1 or one or more pharmaceutically acceptable salts thereof and one or more additional therapeutic agents, optionally together with one or more inert carriers and/or diluents.

13. The pharmaceutical composition according to claim 12 wherein the one or more additional therapeutic agents is selected from the group consisting of antidiabetic agents, agents for the treatment of overweight and/or obesity, and agents for the treatment of high blood pressure, heart failure and/or atherosclerosis.

14. A compound with the structure and stereochemistry as shown in the following formulae:

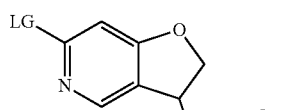

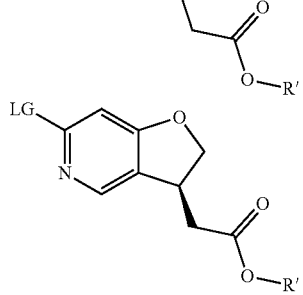

-continued
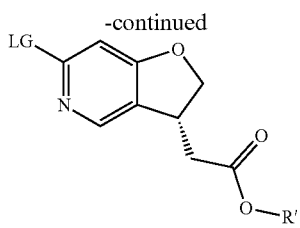
wherein R' is H or $C_{1-4}$-alkyl, and
LG is F, Cl, Br, or I,
or a salt thereof.
* * * * *